(12) United States Patent
Kim et al.

(10) Patent No.: US 8,551,783 B2
(45) Date of Patent: Oct. 8, 2013

(54) EFFICIENT AND UNIVERSAL METHOD FOR NEURAL DIFFERENTIATION OF HUMAN PLURIPOTENT STEM CELLS

(75) Inventors: Dong-Wook Kim, Seoul (KR); Dae-Sung Kim, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 172 days.

(21) Appl. No.: 13/054,692

(22) PCT Filed: Aug. 31, 2010

(86) PCT No.: PCT/KR2010/005892
§ 371 (c)(1),
(2), (4) Date: Jan. 18, 2011

(87) PCT Pub. No.: WO2011/055899
PCT Pub. Date: May 12, 2011

(65) Prior Publication Data
US 2011/0217774 A1    Sep. 8, 2011

(30) Foreign Application Priority Data
Nov. 6, 2009    (KR) .......................... 10-2009-0107235

(51) Int. Cl.
*C12N 5/00*    (2006.01)
*C12N 5/02*    (2006.01)
*C12N 5/071*    (2010.01)

(52) U.S. Cl.
USPC .......................................... 435/377; 435/368

(58) Field of Classification Search
USPC ................................................ 435/377, 368
See application file for complete search history.

(56) References Cited

PUBLICATIONS

Cao et al. J. of Exp. Zoo., 311A: 368-376, 2009.*
Brevini et al. Theriogenology, 74: 544-550, 2010.*
Paris et al. Theriogenology, 74: 516-524, 2010.*
Li et al., Blood, 98: 335-342, 2001.*
Shiraki et al, Genes to Cells, 13:731-746, 2008.*
Wobus et al. (1997) J MoL Cell Cardiology 29:1525.*
Doetschman et al. (1985) J. Embryol. Exp. Morphology 87:27.*
Xu et al. (2002) Circulation Research 91:50.*
Wobus et al. (1988) Biomed. Biochim Acta 12:965.*
Schuldiner (2000) PNAS 97:11307.*
Kramer et al. (2000) Mech. of Dev. 92:193.*
Johansson et al. (1995) Mol and Cell Biol. 15:141.*
Khoo, Biology of Reproduction, 73: 1147-1156, 2005.*
Smith et al., Developmental Biology, 313: 107-117, 2008, available online Oct. 11, 2007.*
Wada et al., PloS One, 4(8), e6722, pp. 1-12, Aug. 24, 2009.*
Yan et al., Stem Cells, 23: 781-790, 2005.*
Kim et al., Stem Cells Rev. and Rep, 6: 270-281, Jun. 2010.*

* cited by examiner

*Primary Examiner* — Thaian N Ton
(74) *Attorney, Agent, or Firm* — Clark & Elbing LLP

(57) ABSTRACT

The present invention relates to a method for inducing neural differentiation of stem cells. In more detail, the present invention relates to a method for inducing neural differentiation of stem cells by inhibiting both BMP (bone morphogenetic protein) and Activin/Nodal signaling pathways in the stem cells. The present invention allows all types of stem cells to effectively differentiate into neural precursor cells regardless of conventional methods for stem cell differentiation including floating culture and attachment culture. In addition, since the neural precursor cells induced by the present invention may be differentiated into specific cells (e.g., dopaminergic neurons) or oligodendrocytes in higher efficient manner, they may be applied to treatment of incurable nerve diseases (e.g., Parkinson's disease or spinal cord injury) and further provide fundamental data on new drug development.

2 Claims, 20 Drawing Sheets

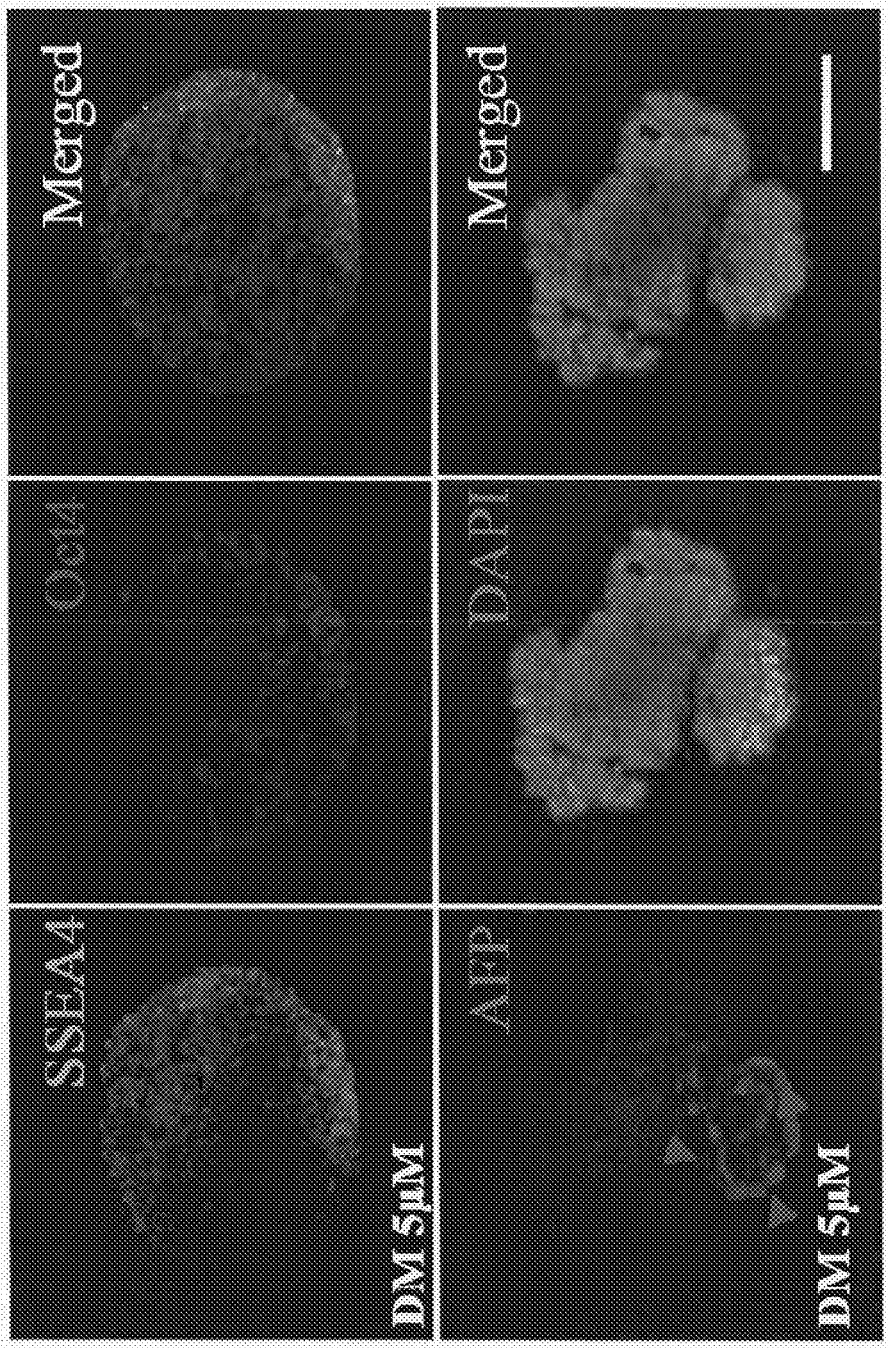

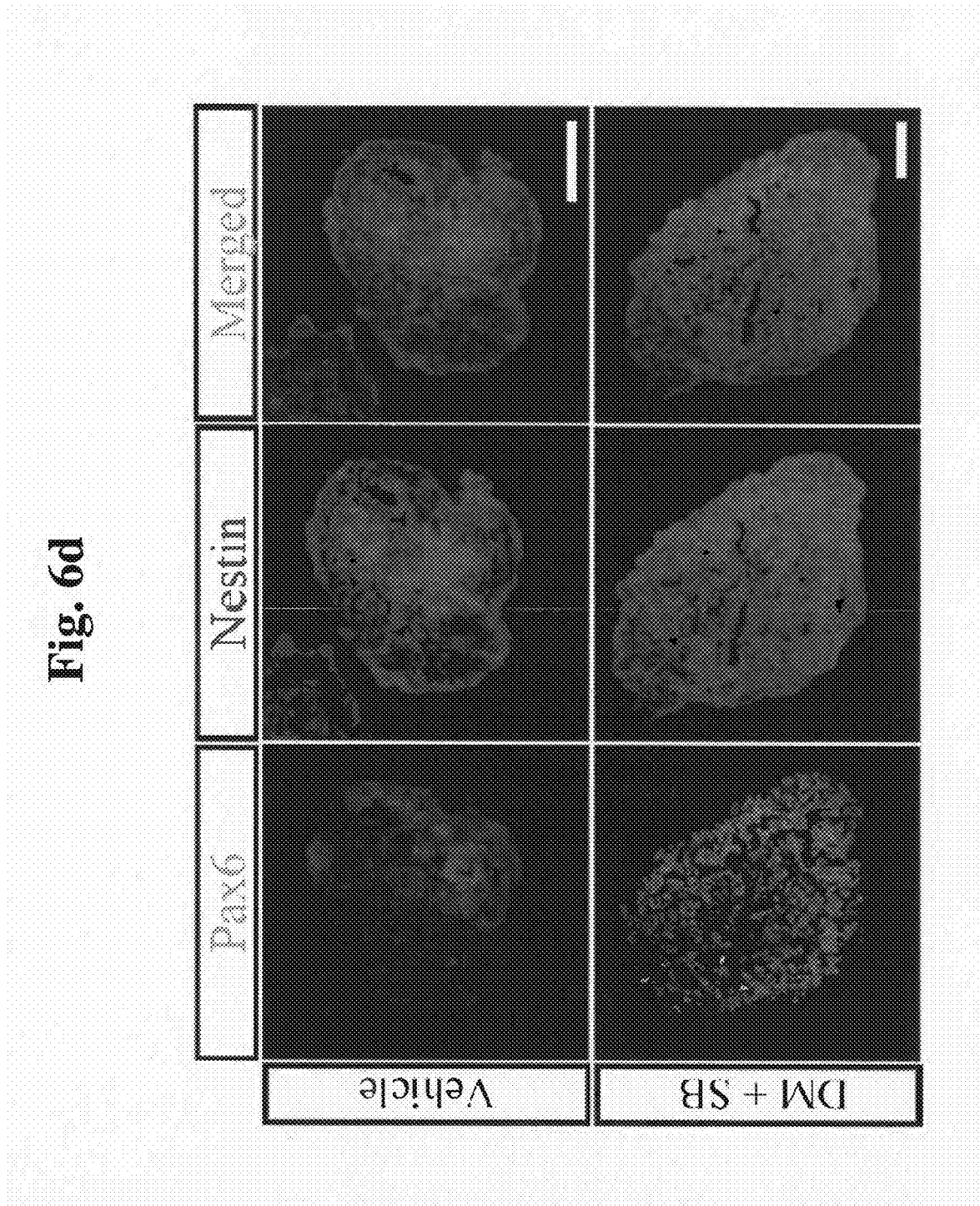

EFFICIENT AND UNIVERSAL METHOD FOR NEURAL DIFFERENTIATION OF HUMAN PLURIPOTENT STEM CELLS

CROSS-REFERENCE TO RELATED APPLICATIONS

This application is the U.S. national stage filing under 35 U.S.C. §371 of international application PCT/KR2010/005892, filed Aug. 31, 2010, which claims benefit of Korean Patent Application 10-2009-0107235, filed Nov. 6, 2009.

BACKGROUND OF THE INVENTION

1. Field of the Invention

The present invention relates to a method for inducing neural differentiation of stem cells. In more detail, the present invention relates to a method for inducing neural differentiation of stem cells by inhibiting BMP (bone morphogenetic protein) and Activin/Nodal signaling pathway in the stem cells.

2. Background of Technique

BMPs (bone morphogenetic proteins) belong to a subfamily of TGF-beta (transforming growth factor-beta) superfamily. TGF-beta pathway plays a central role in diverse signal transduction pathways which regulate growth and differentiation in vertebrates and invertebrates. TGF-beta family is divided into two main groups: (a) BMP group, and (b) TGF-beta/Activin group. Initially, BMPs have been isolated as proteins inducing formation of bone and chondrocyte in a body, and then found to have many regulatory activities during morphogenesis of vertebrate and invertebrate development. Up to now, not less than 30 types of BMPs have been identified in a variety of species including *Drosophila* and *C. elegans* (Ducy P et al, *The family of bone morphogenetic proteins. Kidney Int*, 57 (6):2207-14 (2000)).

Although BMPs have been first found as proteins inducing formation of bone and cartilage in a body, various BMPs have a biologically critical activity in various types of cells including neural cells. For example, BMPs are associated with cell growth and differentiation, apoptosis, neuroectoderm and mesoderm formation, nerve system differentiation (e.g., testis, digestive organs, kidney, lung, teeth, etc.), and right-left asymmetry (Wozney 3M et al. The bone morphogenetic protein family: multifunctional cellular regulators in the embryo and adult. *Eur J Oral Sci.,* 106: 160-6 (1998)).

Activin/Nodal (TGF-β superfamily member) signaling pathway is essential to retain pluripotency in human embryonic stem cells and mouse epiblast stem cells. In addition, Activin/Nodal signaling pathway is important to develop mesoderm in vertebrates.

Stem cells are a generic name for undifferentiated cells of a stage before differentiation toward each cell consisting of tissue, and then differentiated into specific cells by specific differentiation stimuli. Compared to cell division-arrested differentiated cells, stem cells have proliferation (expansion) characteristics capable of producing self-renewal cells via cell division, and may be also differentiated into other lineages by environmental or differential stimuli due to differentiation potential into specific cells by differentiation stimuli, suggesting that stem cells have plasticity to differentiation.

Recently, stem cells have been enormously focused on cell therapeutics. Practically, there have been actively executed many studies for stem cells as cell therapeutics for treating numerous neurological diseases caused by neuron damages. In particular, cranial nerve diseases have been supposed as the most suitable target for cell transplantation treatment than other diseases in the senses that cells externally transplanted are expected to be long-term survival since cranial nerve tissue exhibits almost no immunorejection unlike other tissues.

In this connection, there has been currently attempted to apply stem cells for treating a disorder such as stroke, Alzheimer's disease, Parkinson's disease, demyelinating disease and spinal cordinjury (Isacon O, Deacon T, Trends. Neurosci., 10: 477-482 (1997); Studer et al., Nat. Neurosci., 1: 290-295 (1998)).

Meanwhile, there has been urgently demanded on a technique to differentiate stem cells into specific cells in an effective manner to enhance clinical usefulness of stem cells as cell therapeutics.

WO 2005/003320 discloses a method for neural differentiation of stem cells, and in more detail, a method for inducing stem cells to differentiate into neural cells comprising the steps of: (a) culturing the stem cells with basic fibroblast growth factor; (b) culturing the cells of the step (a) with fibroblast growth factor 8 and Sonic Hedgehog; (c) culturing the cells of the step (b) with brain-derived neurotrophic factor; and d) co-culturing the cells of the step (c) with astrocytes. WO 2004/093812 discloses that a novel class of compounds having particular formula functions as potent inducers of neurogenesis in embryonic stem cells.

WO 2004/05308 discloses a method for preparing dopaminergic cells by interrupting TGF-β signaling pathway in stem cells.

Unfortunately, a technology with higher efficiency to differentiate all stem cells into specific cells (in particular, neural cells) has been not yet reported.

Throughout this application, various publications and patents are referred and citations are provided in parentheses. The disclosures of these publications and patents in their entities are hereby incorporated by references into this application in order to fully describe this invention and the state of the art to which this invention pertains.

DETAILED DESCRIPTION OF THE INVENTION

The present inventors have made intensive studies to develop a method for effectively inducing differentiation of pluripotent stem cells into neural precursor cells in highly efficient manner. As results, we have discovered a method to minimize intricate probability that other cell lineages and undifferentiated cells are contained in cells differentiated from stem cells and to induce directed neural differentiation of stem cells for reducing teratoma development capable of being caused by transplantation.

Accordingly, it is an object of this invention to provide a method for inducing neural differentiation of stem cells.

It is another object of this invention to provide a composition for inducing neural differentiation of stem cells.

Other objects and advantages of the present invention will become apparent from the following detailed description together with the appended claims and drawings.

In one aspect of this invention, there is provided a method for inducing neural differentiation of stem cells, comprising the steps of: (a) inhibiting BMP (bone morphogenetic protein) and Activin/Nodal signaling pathway in the stem cells; and (b) culturing the stem cells.

In another aspect of this invention, there is provided a composition for inducing neural differentiation of stem cells, comprising an inhibitor to BMP (bone morphogenetic protein) and an inhibitor to Activin/Nodal signaling pathway.

The present inventors have made intensive studies to develop a method for effectively inducing differentiation of pluripotent stem cells into neural precursor cells in highly efficient manner. As results, we have discovered a method to minimize intricate probability that other cell lineages and undifferentiated cells are contained in cells differentiated from stem cells and to induce a directed neural differentiation of stem cells for reducing teratoma development capable of being caused by transplantation.

The term "directed neural differentiation of stem cells" used herein includes not only a complete differentiation of stem cells into specific cells but also neural precursor cells to be formed in an intermediate stage before complete differentiation. In other words, the method of the present invention for inducing a directed differentiation of stem cells not only contributes to a complete differentiation of stem cells into specific cells in an effective manner, but also has much higher efficiency on formation of neural precursor from stem cells. Specifically, the method of the present invention to form neural precursors using inhibition of BMP and Activin/Nodal signaling pathway has no technical limitation and may be used together with conventional methods to differentiate neural precursor in a highly efficient manner.

The stem cells capable of being differentiated by the present invention are not restricted, and cells to which the present invention may be applied have properties of stem cells: (a) undifferentiation; (b) potential for indefinite proliferation; and (c) differentiation capacity into specific cells. Stem cells include embryonic stem cells, adult stem cells, induced pluripotent stem cells, embryonic germ cells and embryonic tumor cells, and preferably, embryonic stem cells and induced pluripotent stem cells. The term "induced pluripotent stem cells" used herein refers to one type of pluripotent stem cells artificially derived from non-pluripotent cells (e.g., somatic cells) by insertion of a specific gene. In general, it has been accepted in the art that the induced pluripotent stem cells are equivalent to pluripotent stem cells (e.g., embryonic stem cells), given that the induced pluripotent stem cells have the characteristics of: (a) stem cell gene and protein expression; (b) chromosome methylation; (c) doubling time; (d) embryo formation; (e) teratoma formation; (f) viable chimera formation; (g) hybridoma; and (h) differentiation.

As demonstrated in Examples below, it is one of the advantages of the present invention to provide an universal differentiation protocol capable of being applied to all types of stem cells including embryonic stem cells and induced pluripotent stem cells.

According to the present invention, BMP and Activin/Nodal signaling pathway is blocked for neural differentiation of stem cells.

A substance to block BMP signaling pathway includes various BMP signaling pathway inhibitors known to those ordinarily skilled in the art. The term "an an inhibitor to BMP signaling pathway" used herein refers to a substance which inhibits preferably BMP in itself or binding of BMP to a BMP receptor. The BMP signaling pathway inhibitor utilized in the present invention preferably includes dorsomorphin, Smad6, Smad7, Noggin, Chordin, Gremlin, Sog (short gastrulation), Follistatin, DAN (differential screening-selected gene aberrant in neuroblastoma), Cerberus, Dante or PRDC (Protein Related to DAN and Cerberus). More preferably, the BMP signaling pathway inhibitor includes dorsomorphin, Noggin, Chordin or Gremlin, much more preferably dorsomorphin or Noggin, and most preferably, dorsomorphin.

To block BMP signaling pathway of stem cells in the present invention, a suitable concentration of dorsomorphin is in a range of preferably 1-20 μM, more preferably 3-10 μM, and most preferably, 4-6 μM.

A substance to inhibit Activin/Nodal signaling pathway includes various Activin/Nodal signaling pathway inhibitors known to those skilled in the art. The term "Activin/Nodal signaling pathway" used herein refers to Activin signaling pathway and/or Nodal signaling pathway. The term "an an inhibitor to Activin/Nodal signaling pathway" used herein means a substance which inhibits preferably Activin/Nodal in itself or binding of Activin/Nodal to a Activin/Nodal receptor. The Activin/Nodal signaling pathway inhibitor utilized in the present invention preferably includes inhibitors selected from the group consisting of 4-(5-benzo[1,3]dioxol-5-yl-4-pyridin-2-yl-1H-imidazol-2-yl)benzamide, Smad6, Smad7 and Follistatin, thereby inhibiting Activin/Nodal signaling pathway. More preferably, the inhibitor includes 4-(5-benzo[1,3]dioxol-5-yl-4-pyridin-2-yl-1H-imidazol-2-yl)benzamide or Smad7, and most preferably, a compound with low molecular weight such as 4-(5-benzo[1,3]dioxol-5-yl-4-pyridin-2-yl-1H-imidazol-2-yl)benzamide, not a protein, which has been known as SB431542 in the art. The above-mentioned compound treatment is more efficient than protein treatment.

To inhibit Activin/Nodal signaling pathway of stem cells in the present invention, a suitable concentration of 4-(5-benzo[1,3]dioxol-5-yl-4-pyridin-2-yl-1H-imidazol-2-yl)benzamide is in a range of preferably 1-50 μM, more preferably 5-30 μM, much more preferably 8-20 μM, and most preferably, 9-11 μM.

The above-described 4-(5-benzo[1,3]dioxol-5-yl-4-pyridin-2-yl-1H-imidazol-2-yl)benzamide is represented by the following formula 1:

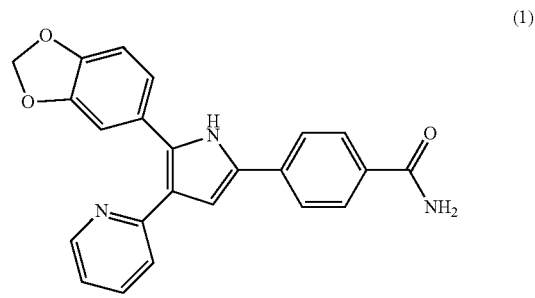 [SMILES: NC(=O)c1ccc(-c2cc(-c3ccccn3)c(-c3ccc4c(c3)OCO4)[nH]2)cc1]

(1)

In detailed description of the present invention, the compound represented by the formula 1 may be interchangeably used with SB431542.

According to a preferable embodiment, the step (a) is performed by culturing the stem cells during embryogenesis or a culture process of formed embryos, and further includes the step in which the embryos in which a neuroectoderm is highly developed by the step (a) are formed.

According to a preferable embodiment, the step (b) to culture further includes the steps of: (b-1) proliferating neural precursor cells by culturing in the presence of bFGF (basic fibroblast growth factor) the embryos in which the neuroectoderm is highly developed; (b-2) inducing dopamine precursor cells by culturing the neural precursor cells in the presence of Sonic hedgehog (Shh) and FGF 8 (fibroblast growth factor 8); and (b-3) forming dopaminergic neurons by culturing the dopamine precursor cells in the presence of glial-derived neurotrophic growth factor (GDNF), brain-derived neurotrophic factor (BDNF) and ascorbic acid.

Preferably, the concentration of bFGF added in the step to proliferate the neural precursors is utilized in a range of 5-100 ng/ml, more preferably 10-50 ng/ml, much more preferably 15-30 ng/ml, and most preferably, 19-21 ng/ml.

Preferably, the concentration of Sonic hedgehog added in the step to proliferate the dopaminergic precursors is utilized in a range of 50-500 ng/ml, more preferably 100-300 ng/ml, much more preferably 150-250 ng/ml, and most preferably, 190-210 ng/ml.

The concentration of FGF8 added in the step to proliferate the dopaminergic precursors is utilized in a range of preferably 10-300 ng/ml, more preferably 50-100 ng/ml, much more preferably 80-150 ng/ml, and most preferably, 90-110 ng/ml.

Preferably, the concentration of BDNF added in the step to form the dopaminergic neurons is utilized in a range of 5-100 ng/ml, more preferably 10-80 ng/ml, much more preferably 15-50 ng/ml, and most preferably, 19-21 ng/ml.

Preferably, the concentration of GDNF added in the step to form the dopaminergic neurons is utilized in a range of 5-100 ng/ml, more preferably 10-80 ng/ml, much more preferably 15-50 ng/ml, and most preferably, 19-21 ng/ml.

The concentration of GDNF added in the step to form the dopaminergic neurons is utilized in a range of preferably 50-500 ng/ml, more preferably 100-300 ng/ml, much more preferably 150-250 ng/ml, and most preferably, 190-210 ng/ml.

According to a preferable embodiment, the expression of Son, Pax6 and Nestin are much highly increased in the neural differentiation of stem cells in the present invention compare to those treated without dorsomorphin and 4-(5-benzo[1,3]dioxol-5-yl-4-pyridin-2-yl-1H-imidazol-2-yl)benzamide.

According to a preferable embodiment, the expression of Id1, Id3, GCM1 and GATA2 are significantly reduced in the neural differentiation of stem cells in the present invention compare to those treated without dorsomorphin and 4-(5-benzo[1,3]dioxol-5-yl-4-pyridin-2-yl-1H-imidazol-2-yl)benzamide.

According to the present invention, it may be possible to differentiate various stem cells (e.g., embryonic stem cells and induced pluripotent stem cells) into similar level of dopaminergic neurons.

Neural cells obtained by the present invention may be applied to treat neurodegenerative disorders, for example including Alzheimer's disease, Huntington's disease, Parkinson's disease, demyelinating disease and amyotrophic lateral sclerosis.

The features and advantages of this invention are summarized as follows:

(a) The present invention provides a method and a composition for inducing neural differentiation of stem cells.

(b) The present invention allows all types of stem cells to effectively differentiate into neural precursor cells regardless of conventional methods for stem cell differentiation including floating culture and attachment culture.

(c) In addition, since the neural precursor cells induced by the present invention may be differentiated into specific cells (e.g., dopaminergic neurons) or oligodendrocytes in higher efficient manner, they may be applied for treatment of incurable nerve diseases (e.g., Parkinson's disease or spinal cord injury) and further provide fundamental data on new drug development.

BRIEF DESCRIPTION OF THE DRAWINGS

FIG. 1a represents expression levels of representative neuroectoderm (Sox1), and FIG. 1b represents expression levels of representative mesoderm (Brachury). FIG. 1c and FIG. 1d represents expression levels of representative endoderm (GATA4) and undifferentiation marker (Oct4), respectively. The y-axis represents means±s.e.m of relative expression level of each gene over the lowest one (arbitrarily designated as 1) among tested cell lines. Statistical significance was estimated using one-way ANOVA (analysis of variance) test with multiple comparisons among cell lines. To reduce a type I error rate, we applied Bonferroni correction as Post Hoc. Symbol: Miz6, Miz-hES6; Miz4, Miz-hES4; SNU3, SNU-hES3; SNU16, SNU-hES16; CHA3, CHA-hES3; BJ1-12, BJ1-iPS12; MSC2-3, MSC-iPS2-3; dH1f2-2, dH1f-iPS2-2.

FIG. 2a shows that expression levels of Id1 and Id3 genes, indicators of BMP signaling activity, was decreased by the treatment of DM (0.1-5 μM) in a dose-dependent manner. One μg/ml of Noggin was used as a positive control. FIG. 2b represents that expression levels of neuroectodermal markers (Pax6 and Nestin) were increased by the 4-day treatment of DM. The y-axis in the graphs represents the relative expression level of each gene after DM- or noggin-treatment compared to DMSO (dimethyl sulfoxide)-treatment. Symbol: DM, dorsomorphin; NOG, noggin (*$p<0.05$, ** $p<0.01$ compared with control group, ANOVA test).

FIG. 4b represents a percentage of colonies with neural rosette structure after neural differentiation of 5 hPSC cell lines in the presence or absence of DM and SB431542. FIG. 4c is qRT-PCR representing that the expression of neuroectoderm markers (SoX1, Pax6 and Nestin) is significantly increased in chemical (DM+SB431542)-treated Miz-hES4, BJ1-iPS12 and MSC-iPS2-3 cells compared to vehicle (DMSO)-treated cells in induction of differentiation. On the contrary, the expression of endoderm, mesoderm, trophoblast and undifferentiated markers was reduced in chemical (DM+SB431542)-treated Miz-hES4, BJ1-iPS12 and MSC-iPS2-3 cells compared to vehicle (DMSO)-treated cells. The relative fold increase of gene expression in chemical (DM+SB431542)-treated group over vehicle (DMSO)-treated group was represented on a logarithmic scale. At least three experiments were carried out (Scale bar: 20 μm).

Figure 5A:
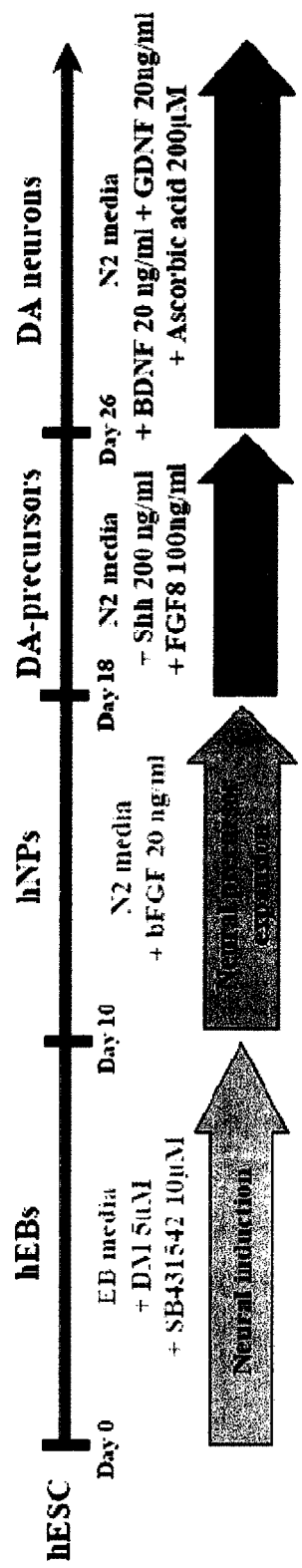
Figure 5B:
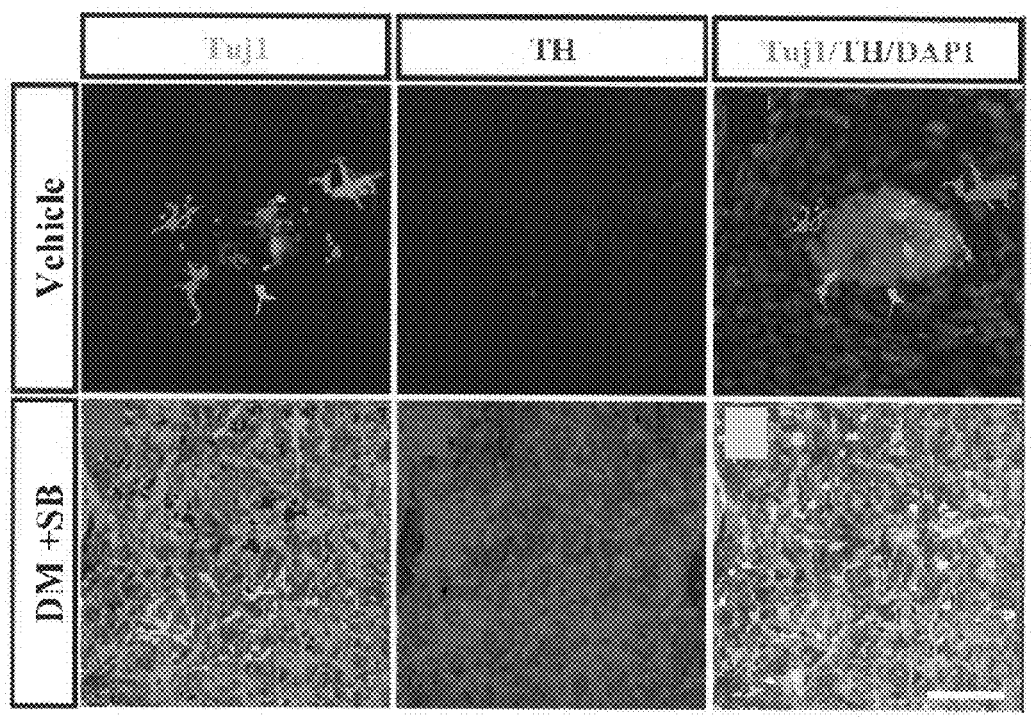
Figure 5C:
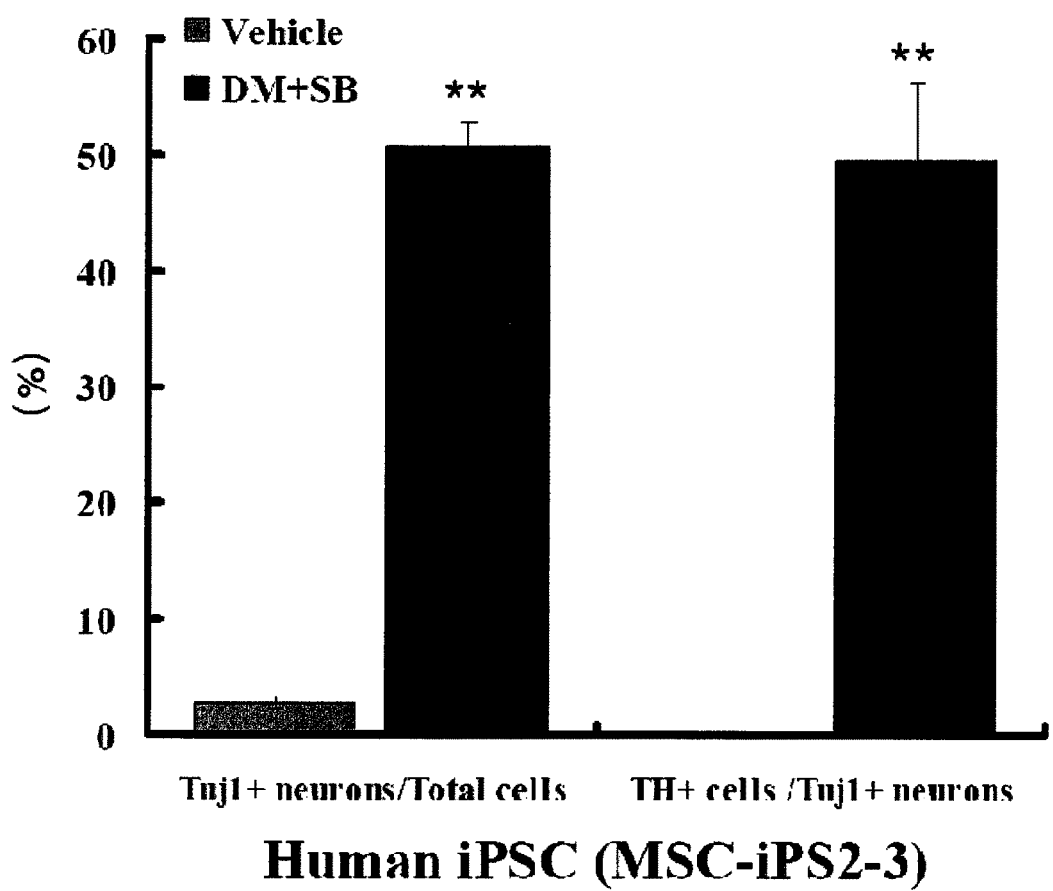

FIGS. 5a-5c show effective differentiation of NPs produced by inhibition of BMP and Activin/Nodal pathway into DA neurons. FIG. 5a schematically represents a differentiation protocol toward DA neuron. FIG. 5b shows that the number of Tuj1- and TH-positive neurons (expressing a tyrosine hydroxylase which synthesizes dopamine) is remarkably increased in chemical (DM+SB431542)-treated group compared to vehicle (DMSO)-treated group using immunocytochemical analyses. FIG. 5c represents marked increase in the number of Tuj1-positive neural cells from the (DM+SB431542)-treated human iPSC (MSC-iPS2-3) cells (50.7±2.2% of total cells) compared to the vehicle (DMSO)-treated cells (2.6±0.5% of total cells). The cell number of each (DM+SB431542)- and vehicle (DMSO)-treated group is 17,711 and 9,233, which is calculated from three independent experiments. Most Tuj1-positive cells (49.5±6.8%) are $TH^+$ neurons. $TH^+$ neurons were almost not detected in DMSO-treated control group (** $p<0.01$; Scale bar, 50 μm).

Figure 6A:
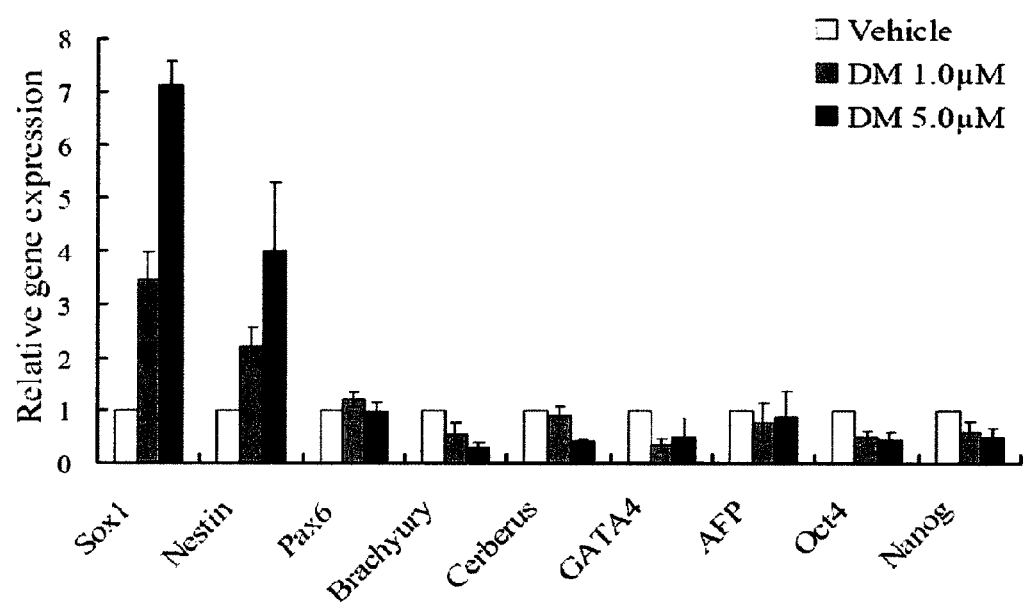
Figure 6C:
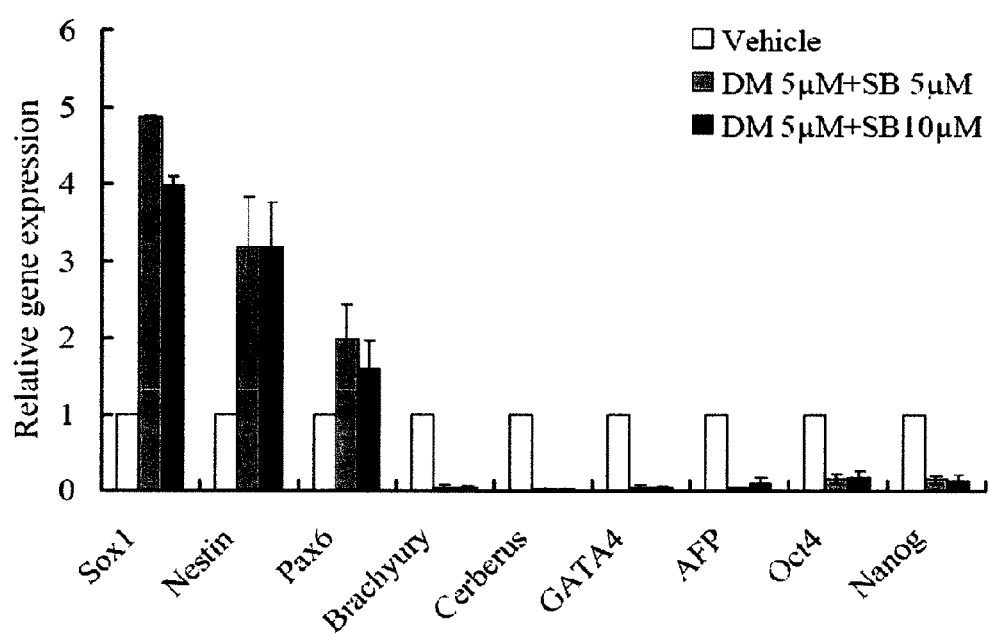

FIGS. 6a-6d shows differentiation of hESCs (H9) into neuroectodermal lineage by modulation of both BMP and Activin/Nodal signal pathways. FIG. 6a represents that the expression of neuroectoderm markers (Sox1 and Nestin) is enhanced after culturing EB in EB media treated with DM for 10 days whereas the expression of mesoderm (Brachyury and Cerberus), endoderm (GATA4 and AFP) and undifferentiated markers (Oct4 and Nanog) is inhibited. FIG. 6b is an immunocytochemical analysis showing that undifferentiated cells (double-positive for Oct4 and SSEA4) and endoderm cells (AFP-positive; red arrowheads) are detected in a portion of EBs treated with 10 μM DM for 10 days. FIG. 6c shows that the expression of neural markers was strikingly enhanced by treatment of both DM and SB431542 for 10 days, whereas the expression of other lineage and undifferentiated markers was significantly reduced. FIG. 6d is an immunocytochemical analysis showing that the expression of Pax6 and Nestin is increased in (DM+SB431542)-treated cells compared to DMSO-treated EBs. The y-axis in graph of FIGS. 6a and 6c represents fold changes in gene expression between chemical-treated and control samples from three independent experiments. DM and SB indicate dorsomorphin and SB431542, respectively. Scale bar, 100 μm.

Figure 7A:
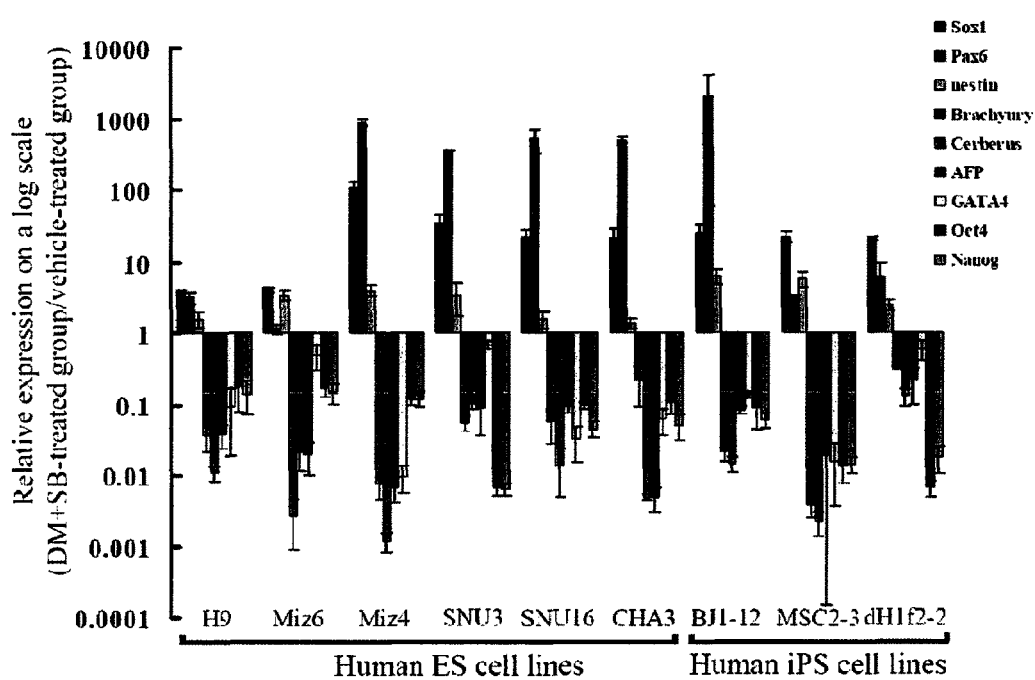
Figure 7B:
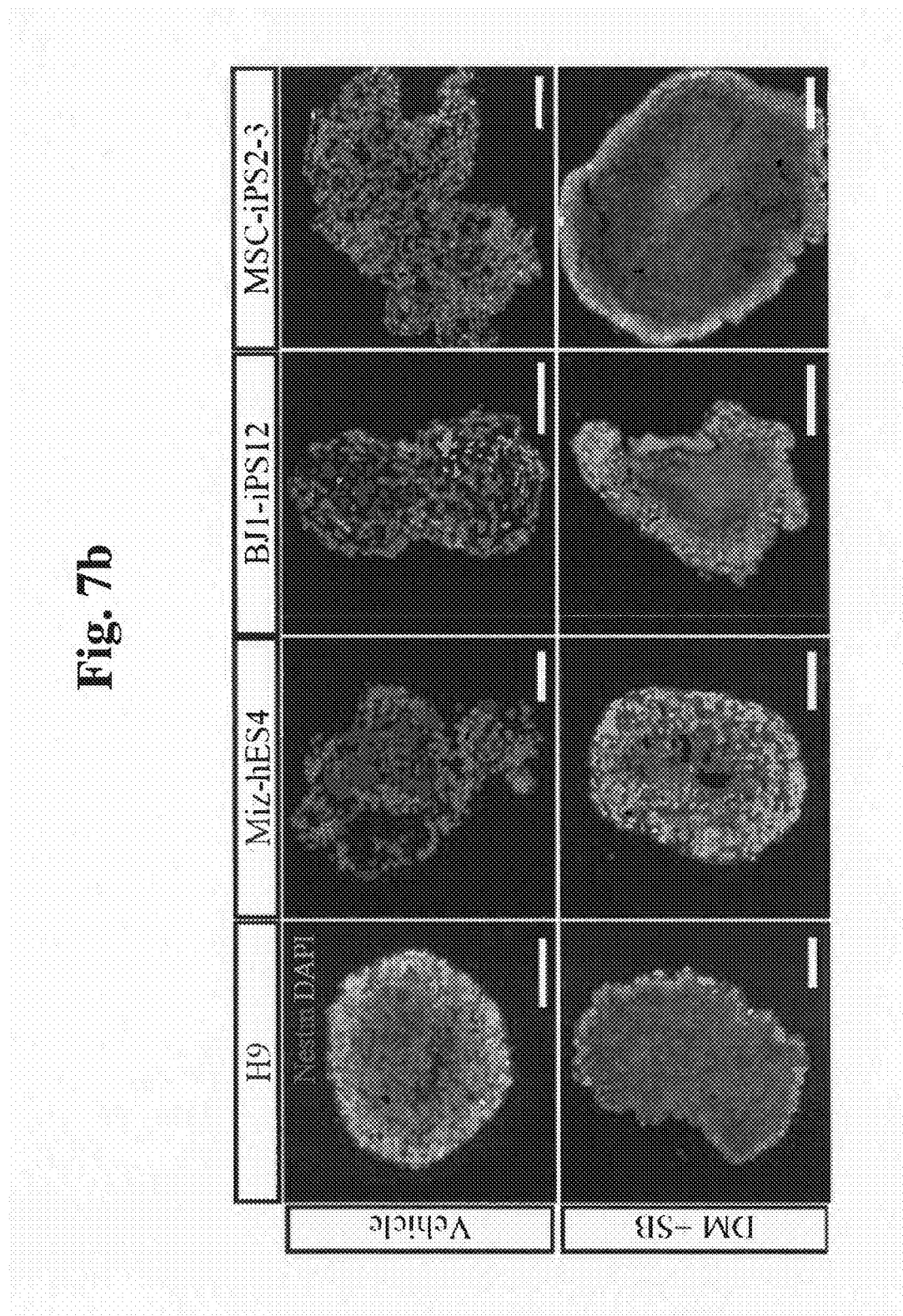

FIGS. 7a-7b represent results to induce neural differentiation of various hPSC cell lines having differentiation propensity by inhibition of both BMP and Activin/Nodal signal pathways. FIG. 7a is a graph representing that the expression of neuroectoderm markers is remarkably increased in chemical (DM+SB431542)-treated hPSC cell lines, whereas the expression of endoderm, mesoderm, trophoblast and undifferentiated markers was significantly reduced in vehicle (DMSO)-treated cells. The y-axis as a log scale shows means±s.e.m of the relative fold increase of gene expression between small molecule-treated and vehicle (DMSO)-treated cells (arbitrarily designated as 1). FIG. 7b is photographs of EB sections from 4 hPSC lines (H9, Miz-hES6, BJ1-iPS12 and MSCiPS2-3) immunostained with anti-Nestin antibody. DM and SB indicate dorsomorphin and SB431542, respectively. Scale bar, 100 μm.

Figure 8:
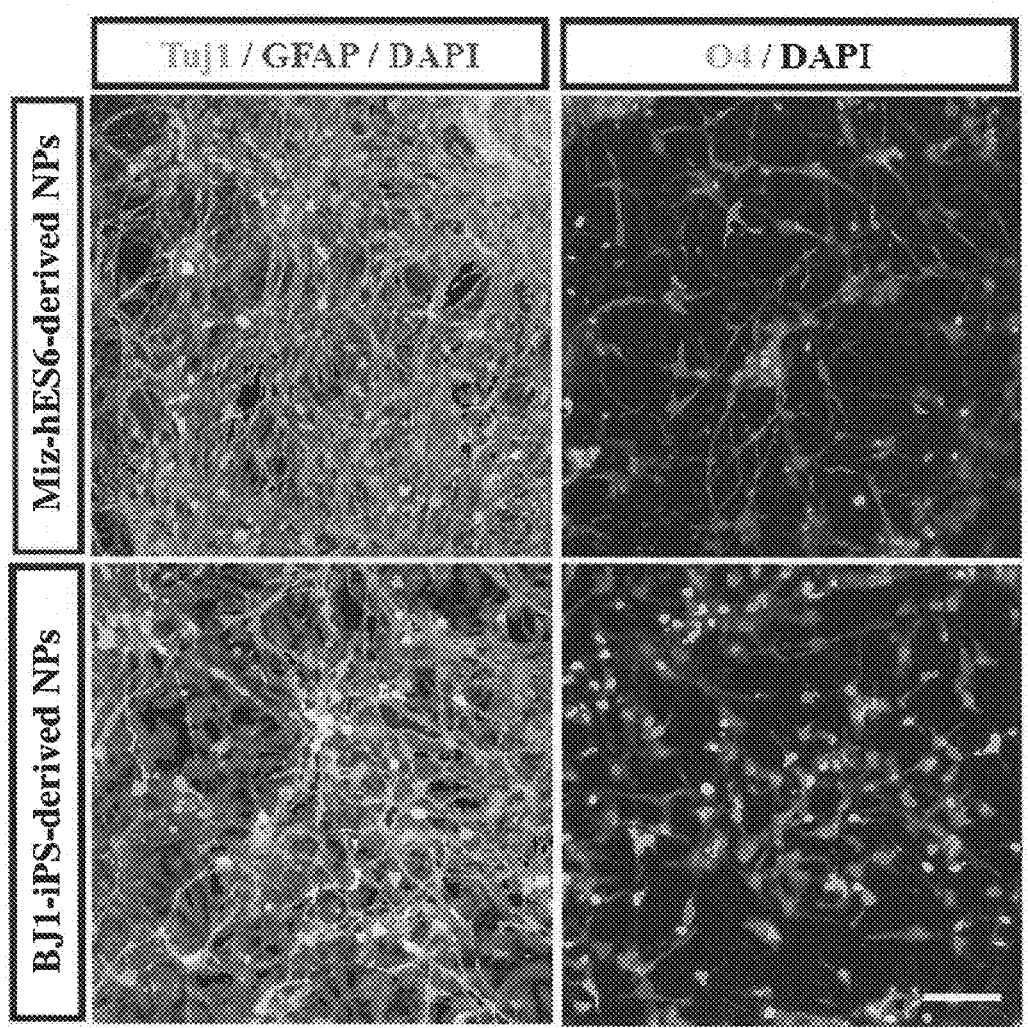

FIG. 8 is an immunostaining analysis showing that NPCs are harvested from human embryonic stem cells (Miz-hES6) and human induced pluripotent stem cells (BJ1-iPS12) by BMP signaling pathway and Activin/Nodal signaling pathway, respectively, inducing differentiation of NPCs into neurons (Tuj1-positive), neuroglial cells (GFAP-positive) and oligodendrocytes (Tuj1-positive). Scale bar, 25 μm.

The present invention will now be described in further detail by examples. It would be obvious to those skilled in the art that these examples are intended to be more concretely illustrative and the scope of the present invention as set forth in the appended claims is not limited to or by the examples.

EXAMPLES

Materials and Methods hESC and hiPSC Culture

The 6 hESC lines used in this study, H9 (P31-45, WiCell Inc, Madison, USA), Miz-hES4 (P67-75) and Miz-hES6 (P34-45) (MizMedi Hospital, Seoul, Korea), CHA-hES3 (P88-93, CHA Hospital, Seoul, Korea), SNU-hES3 (P30-36) and SNU-hES16 (P71-76) (Seoul National University Hospital, Seoul, Korea), were routinely cultured in DMEM-F12 medium supplemented with 20% KSR (Knockout serum replacement; Invitrogen, Carlsbad, USA), 1× non-essential amino acid (Invitrogen), 0.1 mM beta-mercaptoethanol (Sigma, St. Louis, USA), and 4 ng/ml of basic fibroblast growth factor (bFGF; Invitrogen, USA). Most hESC cell lines were grown on the layer of mitotically-arrested mouse embryonic fibroblasts (MEFs; MCTT, Seoul), except SNU-hES3 and SNU-hES16 cell lines which were cultured on STO (ATCC, Manassas, USA) feeder cells. hESC colonies were transferred onto a fresh feeder layer in every 5-7 days by mechanical passaging as previously described [1]. Three human iPSCs, dH1f-iPS2-2, MSC-iPS2-3, and BJ1-iPS12 [2] were from Dr. George Daley's lab at Harvard Medical School and cultured in the same condition as hESCs (See, Nature, 451 (7175): 141-6 (2008); Nat Protoc, 3 (7): 1180-6 (2008)).

Spontaneous Differentiation of hPSC into Neural Cells

EB (embryoid bodies) formation from hESCs and hiPSCs colonies was initiated by detaching the colonies from feeder cells by treatment of 2 mg/ml of type IV collagenase (Invitrogen, USA) for 30 min and transferring the colonies to petri-dish containing normal hESC culture medium without bFGF (EB medium). To examine the effect of dorsomorphin (DM) (also known as Compound C; Sigma, USA) and SB431542 (Calbiochem, San Diego, Calif., USA) in spontaneous differentiation, various concentrations of DM and SB431542 were added in the EB medium during the 10-day EB culture with medium change every 2 days. The expression of several markers was analyzed by qRT-PCR and immunocytochemistry.

Spontaneous Differentiation of hPSC into DA (Dopaminergic) Neurons

After spontaneous differentiation for 10 days, neural precursor cells (NPCs) formed in EBs were expanded in suspension culture in N2 medium (DMEM-F12 & 1×N2 supplement, Invitrogen) containing bFGF (20 ng/ml, Invitrogen) for additional 8-10 days with changing of medium every other day. The expanded NPCs were then triturated with gentle pipetting and seeded on Matrigel (BD Scientific, Bedford, USA)-coated cover-slips with a density of $0.5-2\times10^6$ cells/$cm^2$. Afterwards, DA precursor cells were cultured for 8 days in N2 medium supplemented with N2 medium containing 500 ng/ml of Sonic hedgehog (Shh; R&D Systems, Minneapolis, Minn., USA) and 100 ng/ml of FGF8 (fibroblast growth factor 8; R&D Systems). For dopaminergic maturation, DA precursor cells were performed in DMEM/F12 media supplemented with 1×N2, 20 ng/ml glial-derived neurotrophic factor (GDNF; R&D Systems), 20 ng/ml brain-derived neurotrophic factor (BDNF; R&D Systems) and 200 µM ascorbic acid (Sigma).

Directed Neural Differentiation of hPSCs

Directed differentiation of hPSCs into neural lineage cells was performed using the previously reported method with minor modification [3]. Briefly, EBs were cultured in suspension for 4 days in EB medium with and without 5 µM DM and 5-10 µM SB431542, and then cultured on Matrigel-coated dish in N2 media supplemented with 20 ng/ml bFGF for additional 6 days. Samples were analyzed by colony counting, immunocytochemistry and qRT-PCR.

Immunostaining and Quantitative Analysis

Cells were fixed in 4% para-formaldehyde/PBS solution for 10 min. EBs were also fixed in the same fixative for 1 hr, cryoprotected with 20% sucrose, frozen in O.C.T. compound (Tissue Tek, Torrance, USA), and sectioned at 10 µm thickness with a cryostat. The sections were permeabilized with 0.1% Triton X-100/PBS (for intracellular markers), blocked with 5% normal donkey serum (Calbiochem, Calif., USA) for 1 hr at room temperature, and then treated with primary antibodies at 4° C. overnight. Primary antibodies used in our study were as follows: Oct4 (1:100 dilution; Santa Cruz Biotechnology, Santa-Cruz, Calif., USA); SSEA4 (1:500 dilution; Santa Cruz Biotechnology); Sox1 (1:200 dilution; Millipore, Billerica, Mass., USA); Pax6 (1:200 dilution; DSHB, Iowa, Iowa, USA), Nestin (1:1000 dilution; Millipore); α-fetoprotein (AFP; 1:100 dilution; Santa Cruz Biotechnology); Tuj1 (1:1000 dilution; Covance, Berkeley, Calif., USA); GFAP (1:300 dilution; Millipore), O4 (1:200 dilution; R&D systems) and tyrosine hydroxylase (TH; 1:500 dilution, Millipore; or 1:300, Pelfreez, Rogers, Ark., USA). After the primary antibody incubation, appropriate fluorescence (Alexa-Fluor®-488 or 594)-tagged secondary antibodies (Molecular Probes, Eugene, Oreg., USA) were used for visualization. Cells were treated with DAPI (4',6-diamidino-2-phenylindole; Vector, Burlingame, Calif., USA) for 5 min during the staining procedure to visualize the nuclei. Cell images were captured with Olympus IX71 microscope and DP71 digital camera, and analyzed by Image-Pro Plus ver5.1 (Media Cybernetics, Silver Spring, Md., USA). Quantitative evaluation was performed by counting immuno-labeled cells or colonies from three independent experiments. Values were expressed as means±s.e.m. Student t-test or one-way ANOVA test using the SPSS software Version 12.0 was used to determine statistical significance.

Quantitative RT-PCR (qRT-PCR) and Data Analyses

Total RNAs were extracted using a Easy-Spin® total RNA purification kit (iNtRON Biotechnology, Seoul, Korea) according to the manufacturer's instructions and then 1 µg of the total RNAs were reverse transcribed with Power cDNA synthesis kit (iNtRON Biotechnology). qRT-PCR was performed using SYBR Premix Ex Taq™ (Takara Bio Inc, Shiga, Japan) and the reaction was carried out using the My-iQ or CFX96 Real Time System (Bio-Rad, Hercules, Calif., USA) under the following conditions; (step 1) 1 min at 95° C.; (step 2) 40 cycles of 20 sec at 95° C., 20 sec at 63° C., and 20 sec at 72° C.; (step 3) final extension for 1 min at 72° C. Expression values (Ct values) of specific marker genes were collected and normalized according to those of β-actin. Then, the normalized expression levels of the markers were compared between chemical-treated samples and vehicle-treated control samples according to the ΔΔCt method [4]. All data were confirmed by at least three independent experiments. The primer sequences are listed in Table 1.

TABLE 1

| Gene | Primer | sequence (5'→3') |
|---|---|---|
| Id-1[20] | Forward | ggtgcgctgtctgtctgag (SEQ ID NO: 1) |
|  | Reverse | ctgatctcgccgttgagg (SEQ ID NO: 2) |
| Id-3[20] | Forward | ctggacgacatgaaccactg (SEQ ID NO: 3) |
|  | Reverse | gtagtcgatgacgcgctgta (SEQ ID NO: 4) |
| Sox1 | Forward | gagattcatctcaggattgagattcta (SEQ ID NO: 5) |
|  | Reverse | ggcctactgtaatcttttctccac (SEQ ID NO: 6) |
| Pax6 | Forward | gcggaagctgcaaagaaata (SEQ ID NO: 7) |
|  | Reverse | tttggctgctagtctttctcg (SEQ ID NO: 8) |
| Nestin | Forward | tgcgggctactgaaaagttc (SEQ ID NO: 9) |
|  | Reverse | aggctgagggacatcttgag (SEQ ID NO: 10) |
| Brachyury | Forward | aggtacccaaccctgagga (SEQ ID NO: 11) |
|  | Reverse | gcaggtgagttgtcagaataggt (SEQ ID NO: 12) |
| Cerberus[21] | Forward | acagtgcccttcagccagact (SEQ ID NO: 13) |
|  | Reverse | acaactattttcacagccttcgt (SEQ ID NO: 14) |
| AFP | Forward | tgcaaacgatgaagcaagag (SEQ ID NO: 15) |
|  | Reverse | aacaggcctgagaaatctgc (SEQ ID NO: 16) |
| GATA4 | Forward | gtcatctcactacgggcaca (SEQ ID NO: 17) |
|  | Reverse | cttcagggccgagaggac (SEQ ID NO: 18) |
| Sox17 | Forward | ggcgcagcagaatccaga (SEQ ID NO: 19) |
|  | Reverse | ccacgacttgcccagcat (SEQ ID NO: 20) |
| GCM1[22] | Forward | ctctgaagctcatcccttgcc (SEQ ID NO: 21) |
|  | Reverse | tggacgccttcctggaaagac (SEQ ID NO: 22) |
| GATA2[22] | Forward | agaaccgaccactcatcaagcc (SEQ ID NO: 23) |
|  | Reverse | tgctcttcttggacttgttggac (SEQ ID NO: 24) |
| Oct4 | Forward | tgggctcgagaaggatgtg (SEQ ID NO: 25) |

TABLE 1-continued

| Gene | | Primer sequence (5'→3') |
|---|---|---|
| | Reverse | gcatagtcgctgcttgatcg (SEQ ID NO: 26) |
| Nanog | Forward | ccaacatcctgaacctcagc (SEQ ID NO: 27) |
| | Reverse | gctattcttcggccagttgt (SEQ ID NO: 28) |
| B-actin | Forward | gctcttttccagccttcctt (SEQ ID NO: 29) |
| | Reverse | cttctgcatcctgtcagcaa (SEQ ID NO: 30) |

The superscript indicates reference contained in Examples of the present invention.

Results

For therapeutic applications, efficient differentiation of hPSCs (i.e., hESCs and human iPSCs) into specific desirable cell types is a prerequisite. A recent report demonstrated that each hESC line has its own differentiation inclination toward specific cell lineages [5]. We could also detect significant differences in differentiation propensity among 6 hESC lines generated by 4 institutions. We further noticed that 3 human iPSC lines derived from different somatic cell types also retained their own potential to be differentiated into specific cell lineages (FIG. 1). Since this innate propensity would often negatively affect differentiation into desired cell lineages, all hESC and iPSC lines might need to be examined for their differentiation propensity so that appropriate cell lines can be chosen for each therapeutic application. Since this screening process is laborious, timeconsuming, and costly, it would be of great benefit if there is a way to induce differentiation of all hPSCs into a specific cell lineage of interest, irrespective of their original differentiation propensity. As a proof-of-principle experiment, we set out to establish a universal protocol that drives all the hPSC lines with various differentiation propensity toward neural lineage (i.e., formation of neural precursors (NPs)). Our strategy to generate such a broadly applicable protocol for neural differentiation was by manipulating signaling pathways critically implicated in embryonic neural induction with small molecules.

Figure 2A:
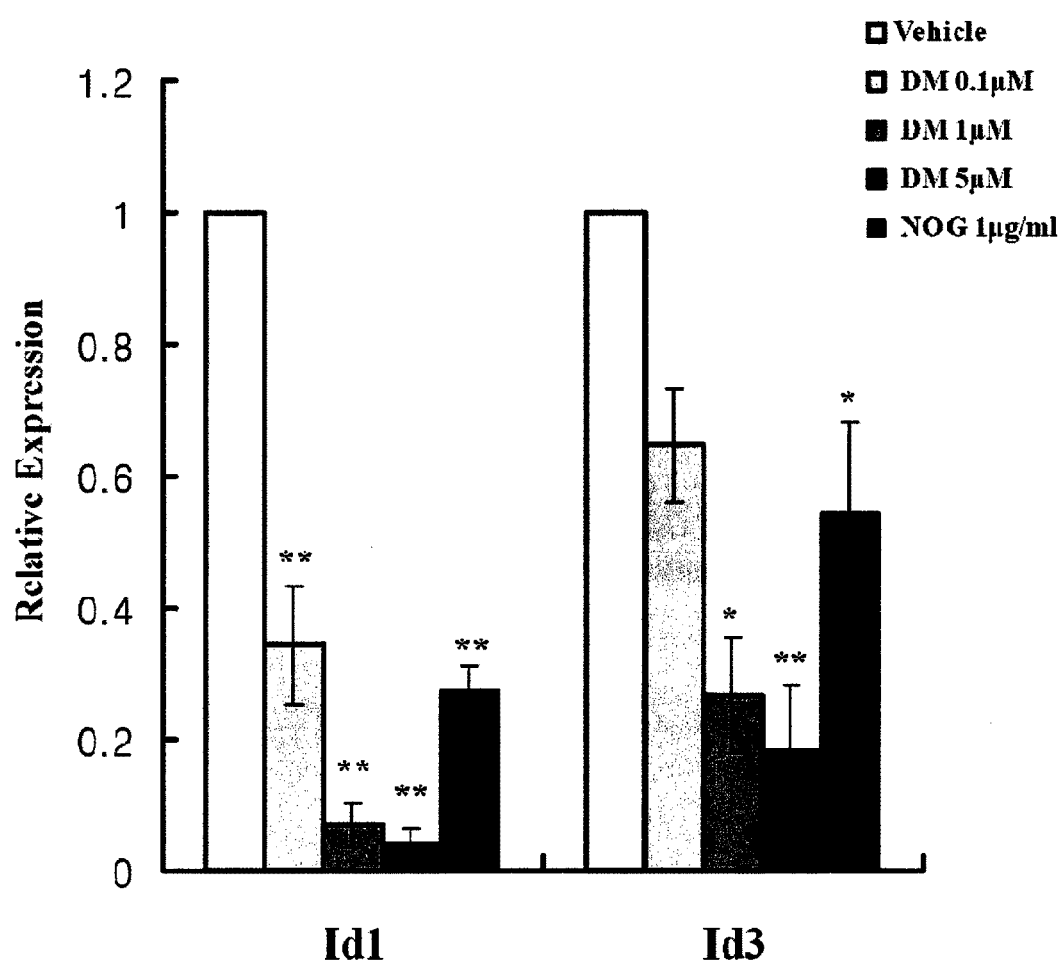
FIGS. 2a-2b represents results reducing neural differentiation of stem cells by treatment of DM which effectively inhibits endogenous BMP signaling cascade. Four days after spontaneous differentiation in the presence or absence of DM, the expression level of several markers was measured from EBs by qRT-PCR.
Figure 2B:
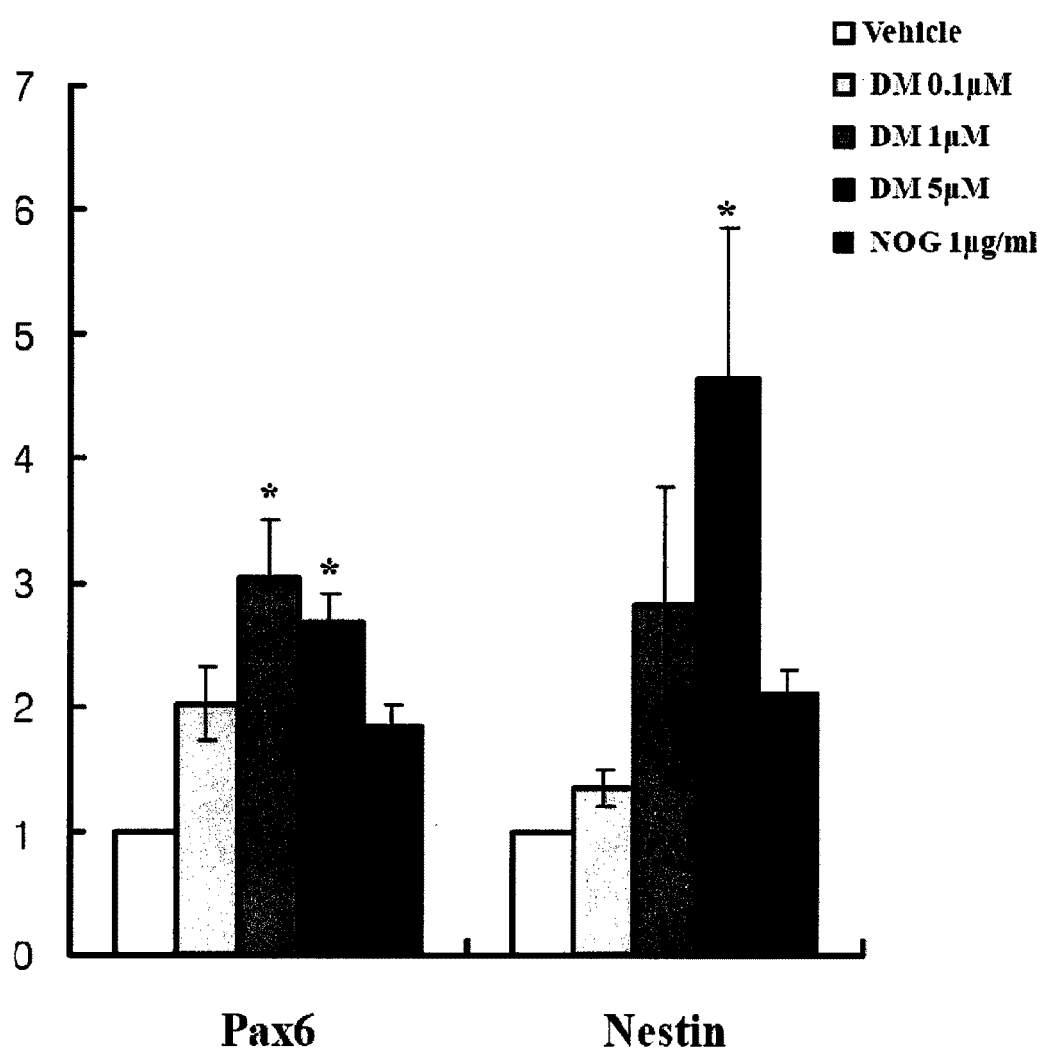

To initiate differentiation, mechanically chopped H9 hESC colony fragments were cultured in suspension as embryoid bodies (EBs). Normally, EBs grown in a spontaneous differentiation condition which does not contain any lineage-inducing growth factor yields low efficiency of neural differentiation, although the efficiency varies depending on the differentiation propensity of each hESC line. In an attempt to promote neural differentiation at the expense of other cell lineages, we first determined to block the bone morphogenetic protein (BMP) signaling pathway during EB formation. Inhibition of the BMP signaling has been known to play a role in neural induction during early embryonic development [6, 7]. To this end, we used dorsomorphin (DM), a selective small molecule BMP antagonist [8], instead of noggin, a polypeptide BMP inhibitor, since small molecules are more readily accessible to the cells inside EBs [9]. We first confirmed the effectiveness of DM by showing that 4 day-treatment of EBs with DM (0.1-5 μM) diminished the expression level of Id1 and Id3 genes, the indicators of BMP signaling activity, in a dose-dependent manner (FIG. 2a). Next, we found that DM-treatment increased neural markers such as Pax6 and Nestin in the differentiating EBs dose-dependently, indicating that inhibition of BMP signaling pathway with DM promotes differentiation of H9 hESCs toward neural lineage (FIG. 2b).

Figure 1A:
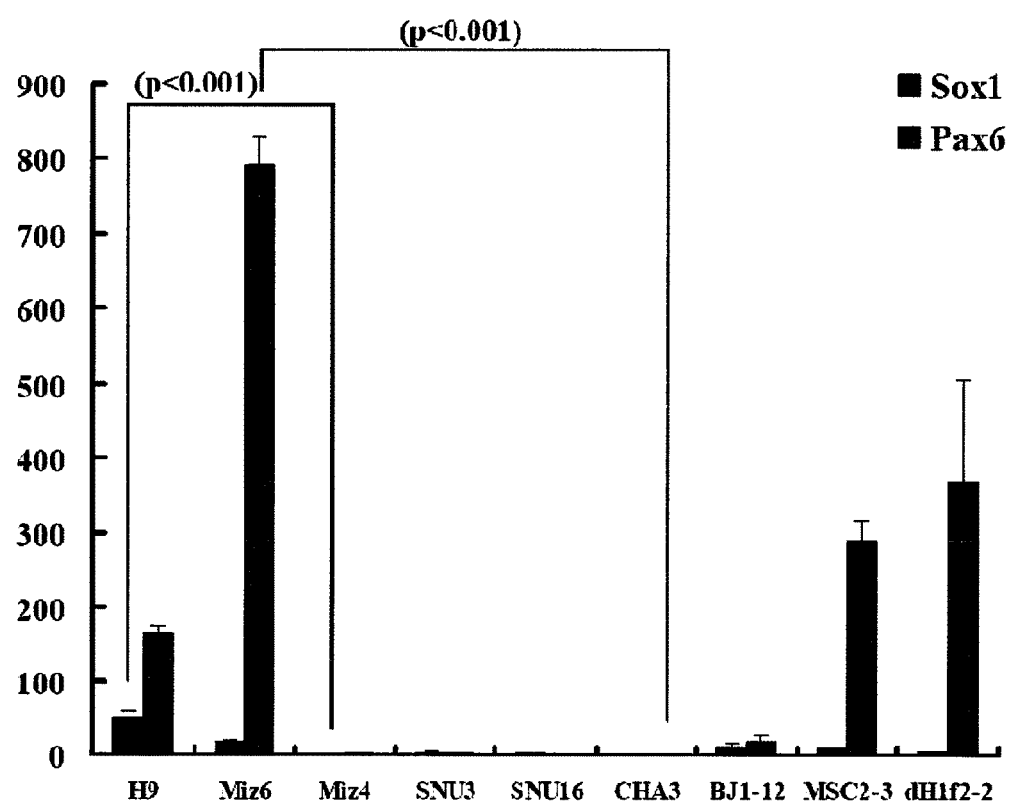
FIGS. 1a-1d represent results examining differentiation propensity of total 6 hESC lines (H9, Miz-hES4 and 6, SNU-hES3 and 16, CHA-hES3) and 3 human iPSC lines (BJ1-iPS12, MSC-iPS2-3, dH1f-iPS2-2) using qRT-PCR.
Figure 1B:
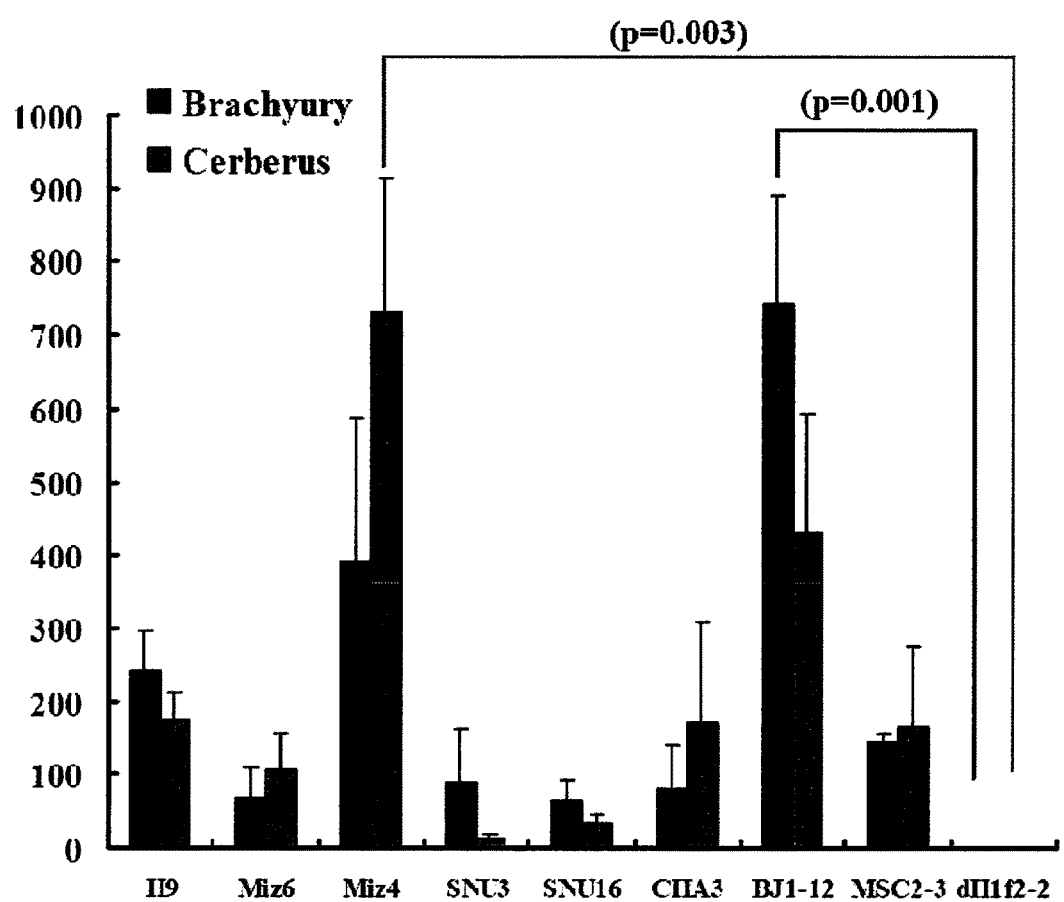
Figure 1C:
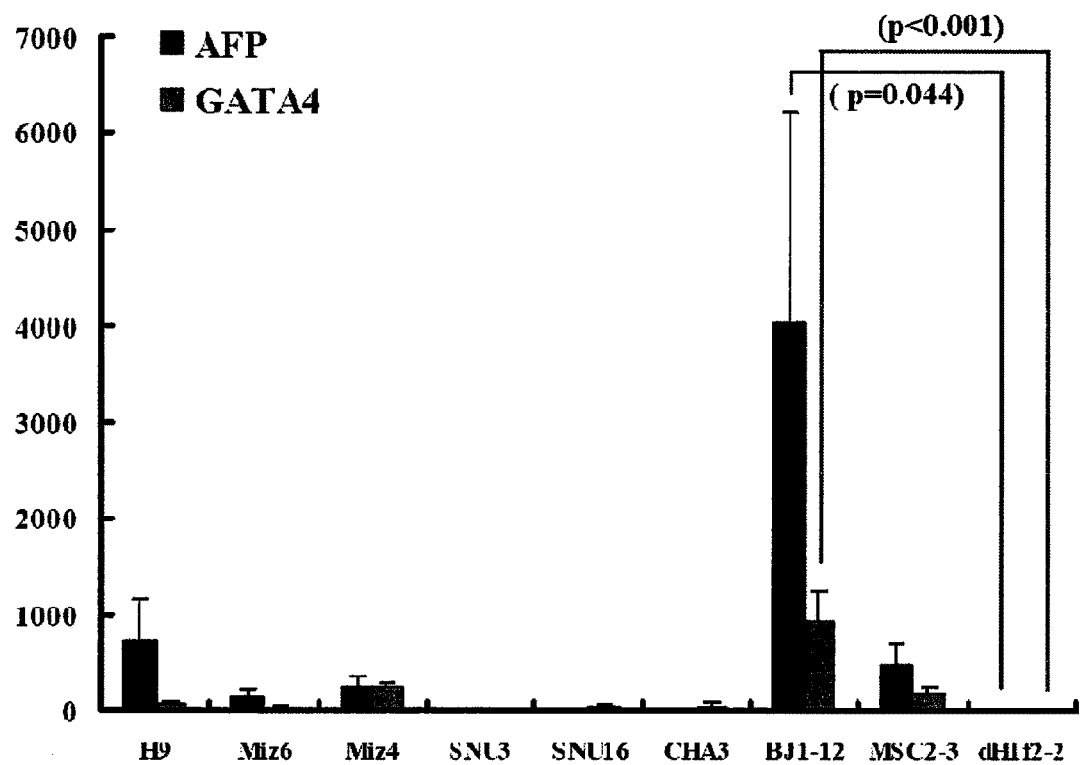
Figure 1D:
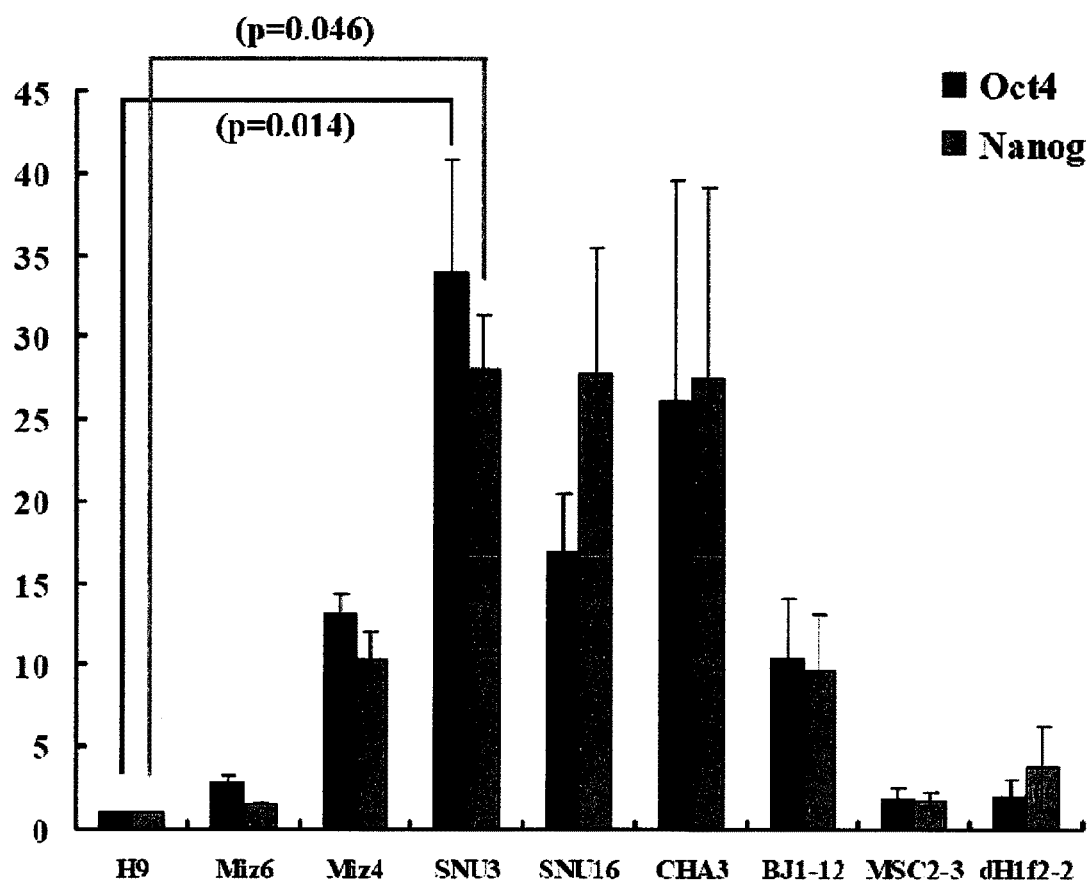

To investigate if the inhibition of BMP pathway sufficiently induces neural differentiation and at the same time reduces differentiation along other lineages, the effects of DM on the fate change of hESCs were more closely examined. In this experiment, EBs were cultured in spontaneous differentiation medium containing DM (1 and 5 μM) for 10 days and expression of representative markers of three germ layers as well as undifferentiated hESCs was examined by quantitative RT-PCR (qRT-PCR) and immunocytochemistry (FIG. 1). The DM-treatment during EB formation significantly enhanced the expression of neural markers (Sox1 and nestin) dose-dependently, while markers for mesoderm (Brachyury, Cerberus), endoderm (alpha-fetoprotein (AFP), GATA4) and undifferentiated hESCs (Oct4 and Nanog) were reduced (FIGS. 1a-1d). However, some endodermal (i.e., AFP) and undifferentiated cell markers (i.e., Oct4 and SSEA4), were still detected (FIGS. 1b-1d). These results implies that blocking BMP pathway alone is not enough to produce highly pure population of neural cells that has minimal contamination of endodermal, mesodermal, and remnant undifferentiated cells. This conclusion prompted us to look for additional signaling pathway the inhibition of which would further enhance the differentiation of hESCs toward neural lineage. Activin/Nodal pathway has been known to play a pivotal role during early embryonic development by inducing endodermal and mesodermal differentiation [10], while suppressing differentiation into neuroectodermal lineage [11, 12]. In addition, recent reports demonstrated that Activin/Nodal signaling is also important for maintaining stemness of hESCs [13, 14]. Therefore, we postulated that blocking of Activin/Nodal signaling would drive differentiation of hESCs more favorably toward neuroectoderm with reduction of the other lineages and undifferentiated cells.

Figure 3:
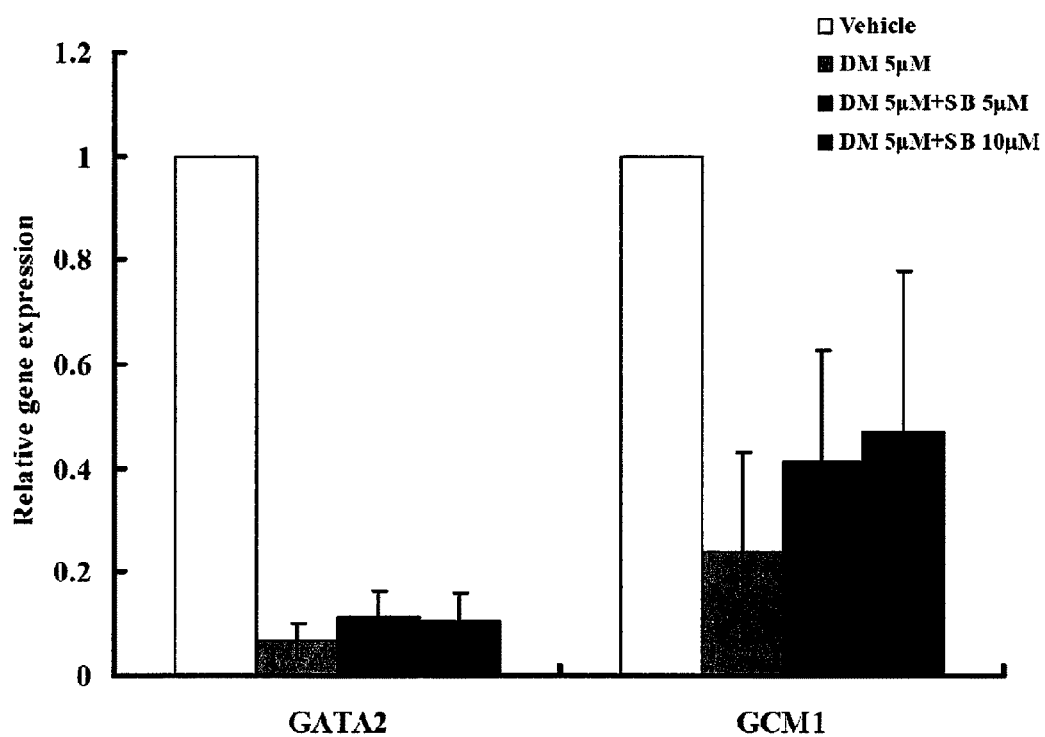
FIG. 3 is a result inhibiting differentiation of hESCs (H9) into trophoblasts by modulation of both BMP and Activin/Nodal signal pathways. EBs were cultured for 10 days with or without DM (5 μM) and SB431542 (5-10 μM) and expression level of two representative trophoblast markers (GATA2 and GCM1) was examined by qRT-PCR.

Based on this idea, we tested if blocking of Activin/Nodal signaling in addition to the inhibition of BMP pathway would lead to further induction of neural cells with reduction of the other unwanted cells down to minimal level. When EBs were cultured in the spontaneous differentiation medium containing both SB431542 (5 or 10 μM), a specific inhibitor to Activin/Nodal signaling, and DM (5 μM), the expression of neural markers (Sox1, Pax6, and Nestin) was significantly enhanced, while both endodermal (AFP and GATA4) and mesodermal (Brachyury and Cerberus) markers were dramatically reduced (FIGS. 1b-1c). More importantly, markers for undifferentiated pluripotent cells (Oct4 and Nanog) were also greatly reduced (FIG. 1d). The increase of neural cells in this experiment was also confirmed by immunocytochemistry (FIG. 1d). Expression of trophoblast markers (GATA2 and GCM1) was also decreased by inhibition of either BMP pathway alone (DM-treatment) or both BMP and Activin/Nodal pathways (DM+SM431542-treatment) (FIG. 3). This result is in line with the previous report that blocking of Activin/Nodal pathway leads to differentiation of hESCs into trophoblasts only when BMP pathway is active [15].

Cumulatively, our data suggested that efficient and exclusive neural induction from hPSCs would require inhibition of both BMP and Activin/Nodal signaling pathways. These results are in line with the recent work showing that simultaneous and continued suppression of BMP and Activin/Nodal signaling is required for neural induction in *Xenopus* embryo development [16].

The next question is whether the simultaneous treatment of DM and SB431542 could direct the fates of both hESC and iPSC lines toward neural lineage, irrespective of their innate differentiation propensity. To this end, EBs generated from 9 hPSC lines (6 hESC lines and 3 human iPSC lines) were treated with both DM (5 µM) and SB431542 (10 µM) during spontaneous differentiation process. Our qRT-PCR analyses demonstrated that treatment with DM and SB431542 significantly enhanced neural induction with concomitant reduction of cells of other lineages (FIG. 2a). Interestingly, the fold increases of neural marker expression between control (vehicle (DMSO)-treated cells) and (DM+SM431542)-treated cells were much higher in the cell lines that had innate differentiation inclination unfavorable to neural fate such as Miz-hES4, SNU-hES3, SNU-hES16, CHA-hES3, and BJ1-iPS12 cells (FIG. 1a and FIG. 2a). Immunocytochemical analyses also clearly demonstrated that more cells expressed nestin, a neural precursor marker, when both BMP and Activin/Nodal signaling pathways were suppressed (FIG. 2b). We have not detected any undifferentiated cells after the DM+SBtreatment by immunocytochemistry (data not shown).

Figure 4A:
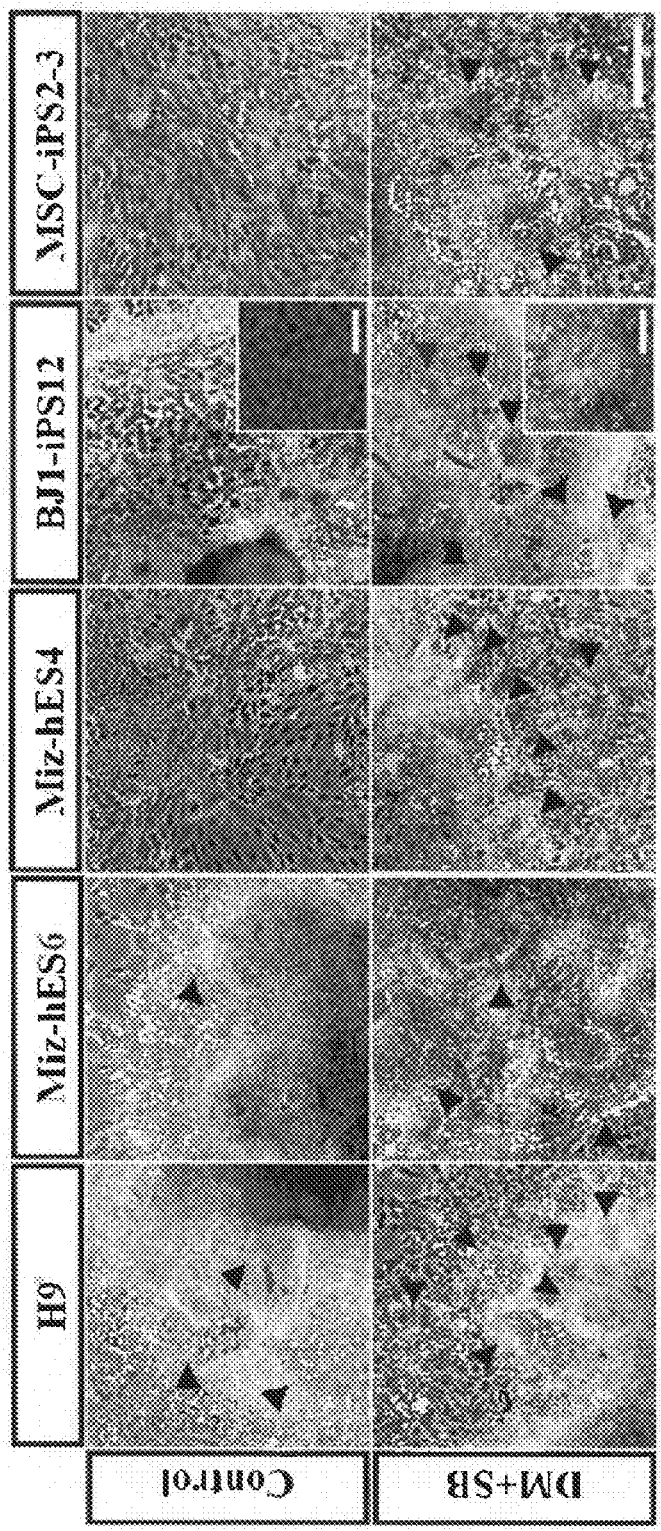
FIGS. 4a-4c represent that the inhibition of both BMP and Activin/Nodal signal pathways significantly promotes differentiation of hESCs (H9) into neuroectodermal lineage, in addition to induced neuron differentiation. After culturing for 4 days with or without DM (5 μM) and SB431542 (5-10 μM), EBs were adhered to a culture dish and further incubated in neural induction media (N2 media supplemented with 20 ng/ml bFGF) for 6 days. H9 and Miz-hES6 were developed to about 90% of numerous colonies with a neural rosette structure (FIGS. 4a-4b). On the contrary, 2.6-25.5% of colonies developed from Miz-hES4, BJ1-iPS12 and MSC-iPS2-3 cells had various non-neural cell shapes with a neural rosette structure. These results demonstrate that differentiation propensity of hPSCs is still maintained after performing induction differentiation protocol as well as spontaneous differentiation (upper panal in FIG. 4a). Surprisingly, chemical treatment (DM and SB431542) to EBs for 4 days leads to induce efficient and equal neural rosette formation in most colonies from the cells used in the experiments (lower panal in FIG. 4a). The neural rosette structures were immunostained with anti-Nestin (green) and anti-Sox1 (red) antibody (see, a photo inserted into BJ1-iPS12 in FIG. 4a).
Figure 4B:
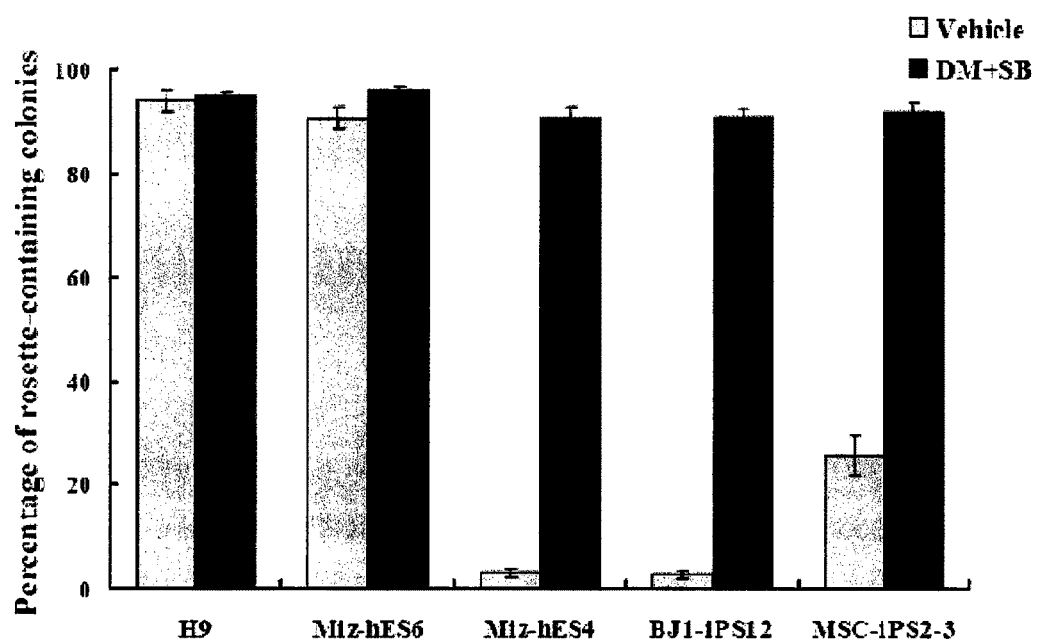
Figure 4C:
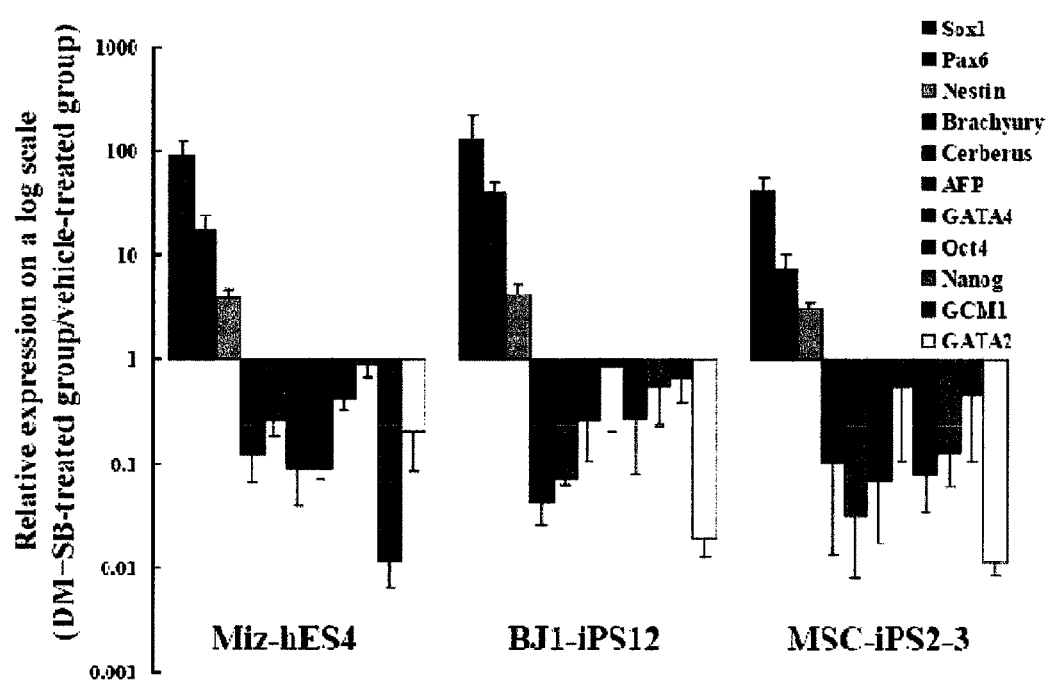

In addition to their effects during spontaneous differentiation, DM and SB431542 also augmented neural cell generation when used with a direct differentiation protocol that had designed to induce neural differentiation from hESCs13 (FIG. 4) [17]. The neural precursors generated in our experiments were shown to retain the multipotency to become neurons, astrocytes, and oligodendrocytes (FIG. 8).

Collectively, these results suggested that significantly different differentiation inclination among hESC and iPSC lines could be efficiently overcome by simultaneous modulation of BMP and Activin/Nodal signaling pathways whether spontaneous or directed differentiation procedure was used: under both conditions, all hPSCs were efficiently fated into neural lineage.

To examine whether the NPs generated by simultaneous blocking of BMP and Activin/Nodal signals retains the capability to become a specified neural sub-type, we attempted further differentiation into dopamine (DA) neurons by modification of existing protocols (FIG. 5) [18, 19]. Immunocytochemical analyses showed marked increase in the number of Tuj1-positive neural cells from the (DM+SB431542)-treated human iPSC (MSC-iPS2-3) cells (50.7±2.2% of total cells) compared to the vehicle-treated cells (2.6±0.5% of total cells) (FIGS. 5b-5h). A significant portion (49.5±6.8%) of the Tuj1-positive cells was TH+ neurons. These data indicated that neural cells generated by the modulation of BMP and Activin/Nodal signaling also retain the capability to differentiate into a specific neural type such as DA neurons.

In summary, we showed in this report that hPSCs with a variety of differentiation propensity can be differentiated efficiently into neural lineage by modulation of BMP and Activin/Nodal pathways. This study suggests that modulation of signaling pathways may be able to overcome the innate differentiation potential of hESCs and human iPSCs. This would simplify the need to generate multiple independent iPSC lines from patients in need of cell replacement therapy.

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCES

1. Oh, S. K. et al. *Stem Cells* 23, 605-609 (2005).
2. Park, I. H. et al. *Nature* 451, 141-146 (2007).
3. Zhang, S. C., Wernig, M., Duncan, I. D., Br, O. & Thomson, J. A. *Nat. Biotechnol* 19, 1129-1133 (2001).
4. Pfaffl, M. W. *Nucleic Acids Res* 29, e45 (2001).
5. Osafune, K. et al. *Nat. Biotechnol.* 26, 313-315 (2008).
6. Wilson, S. I & Edlund, T. *Nat. Neurosci. Suppl,* 1161-1168 (2001).
7. Mu, I. & Brivanlou, A. H. *Nat. Rev. Neurosci.* 3, 271-280 (2002).
8. Yu, P. B. et al. *Nat. Chem. Biol.* 4, 33-41 (2008).
9. Ding, S. & Schultz, R *Nat. Biotechnol.* 22, 833-840 (2004).
10. Schier, A. F. *Annu. Rev Cell Dev. Biol.* 19, 58921 (2003).
11. Vallier, L., Reynolds, D. & Pedersen, R. A. *Dev Biol.* 275, 403-421 (2004).
12. Camus, A., Perea-Gomez, A., Moreau, A. & Collignon, J. *Dev Biol.* 295, 743-755 (2006).
13. Vallier, L., Alexander, M. & Pedersen, R. A. *J. Cell. Sci.* 118, 4495-4509 (2005).
14. Xiao, L., Yuan, X. and Sharkis, S. *J. Stem Cells* 24, 1476486 (2006).
15. Wu, J. et al. *J. Biol. Chem.* 283, 249915002 (2008).
16. Chang, C. & Harland, R. M. Development 134, 3861-3872 (2007).
17. Zhang, S. C., Wernig, M., Duncan, I. D., Br, O. & Thomson, J. A. *Nat. Biotechnol.* 19, 1129-1133.
18. Cho, M. S. et al. *Proc Natl. Acad. Sci. USA.* 105, 3392-3397 (2008).
19. Yan, Y. et al. *Stem Cells* 23, 781-790 (2005)
20. Xu, R-.H. et al. *Nat Methods* 2, 185-190 (2005).
21. Kroon, E. et al. *Nat Biotech* 26, 443-452 (2008).
22. Xiao, L., Yuan, X. and Sharkis, S. *J. Stem Cells* 24, 1476486 (2006).

What is claimed is:

1. A method for inducing neural differentiation of stem cells selected from the group consisting of human embryonic stem cells (hESCs) and human induced pluripotent stem cells (hiPSCs), comprising the steps of
   (a) inhibiting BMP (bone morphogenetic protein) and Activin/Nodal signaling pathway in the stem cells using dorsomorphin and 4-(5-benzo[1,3] dioxol-5-yl-4-pyridin-2-yl-1H-imidazol-2-yl)benzamide; and
   (b) culturing the stem cells, thereby inducing neural differentiation of the stem cells.

2. The method according to claim 1, wherein the step (b) further comprises the steps of: (b-1) proliferating neural precursor cells by culturing in the presence of bFGF (basic fibroblast growth factor) the stem cells obtained in the step (a); (b-2) inducing dopamine precursor cells by culturing the neural precursor cells in the presence of Sonic hedgehog (Shh) and FGF 8 (fibroblast growth factor 8); and (b-3) forming dopaminergic neurons by culturing the dopamine precursor cells in the presence of glial-derived neurotrophic growth factor (GDNF), brain-derived neurotrophic factor (BDNF) and ascorbic acid.

* * * * *

SEQUENCE LISTING

<160> NUMBER OF SEQ ID NOS: 30

<210> SEQ ID NO 1
<211> LENGTH: 19
<212> TYPE: DNA
<213> ORGANISM: Artificial Sequence
<220> FEATURE:
<223> OTHER INFORMATION: Id-1 F-primer

<400> SEQUENCE: 1
ggtgcgctgt ctgtctgag                                                                                   19

<210> SEQ ID NO 2
<211> LENGTH: 18
<212> TYPE: DNA

```
<213> ORGANISM: Artificial Sequence
<220> FEATURE:
<223> OTHER INFORMATION: Id-1 R-primer

<400> SEQUENCE: 2
ctgatctcgc cgttgagg                                                 18

<210> SEQ ID NO 3
<211> LENGTH: 20
<212> TYPE: DNA
<213> ORGANISM: Artificial Sequence
<220> FEATURE:
<223> OTHER INFORMATION: Id-3 F-primer

<400> SEQUENCE: 3
ctggacgaca tgaaccactg                                               20

<210> SEQ ID NO 4
<211> LENGTH: 20
<212> TYPE: DNA
<213> ORGANISM: Artificial Sequence
<220> FEATURE:
<223> OTHER INFORMATION: Id-3 R-primer

<400> SEQUENCE: 4
gtagtcgatg acgcgctgta                                               20

<210> SEQ ID NO 5
<211> LENGTH: 27
<212> TYPE: DNA
<213> ORGANISM: Artificial Sequence
<220> FEATURE:
<223> OTHER INFORMATION: Sox1 F-primer

<400> SEQUENCE: 5
gagattcatc tcaggattga gattcta                                       27

<210> SEQ ID NO 6
<211> LENGTH: 24
<212> TYPE: DNA
<213> ORGANISM: Artificial Sequence
<220> FEATURE:
<223> OTHER INFORMATION: Sox1 R-primer

<400> SEQUENCE: 6
ggcctactgt aatcttttct ccac                                          24

<210> SEQ ID NO 7
<211> LENGTH: 20
<212> TYPE: DNA
<213> ORGANISM: Artificial Sequence
<220> FEATURE:
<223> OTHER INFORMATION: Pax6 F-primer

<400> SEQUENCE: 7
gcggaagctg caaagaaata                                               20

<210> SEQ ID NO 8
<211> LENGTH: 21
<212> TYPE: DNA
<213> ORGANISM: Artificial Sequence
<220> FEATURE:
<223> OTHER INFORMATION: Pax6 R-primer

<400> SEQUENCE: 8
tttggctgct agtctttctc g                                             21
```

```
<210> SEQ ID NO 9
<211> LENGTH: 20
<212> TYPE: DNA
<213> ORGANISM: Artificial Sequence
<220> FEATURE:
<223> OTHER INFORMATION: Nestin F-primer

<400> SEQUENCE: 9
tgcgggctac tgaaaagttc                                              20

<210> SEQ ID NO 10
<211> LENGTH: 20
<212> TYPE: DNA
<213> ORGANISM: Artificial Sequence
<220> FEATURE:
<223> OTHER INFORMATION: Nestin R-primer

<400> SEQUENCE: 10
aggctgaggg acatcttgag                                              20

<210> SEQ ID NO 11
<211> LENGTH: 19
<212> TYPE: DNA
<213> ORGANISM: Artificial Sequence
<220> FEATURE:
<223> OTHER INFORMATION: Brachyury F-primer

<400> SEQUENCE: 11
aggtacccaa ccctgagga                                               19

<210> SEQ ID NO 12
<211> LENGTH: 23
<212> TYPE: DNA
<213> ORGANISM: Artificial Sequence
<220> FEATURE:
<223> OTHER INFORMATION: Brachyury R-primer

<400> SEQUENCE: 12
gcaggtgagt tgtcagaata ggt                                          23

<210> SEQ ID NO 13
<211> LENGTH: 21
<212> TYPE: DNA
<213> ORGANISM: Artificial Sequence
<220> FEATURE:
<223> OTHER INFORMATION: Cerberus F-primer

<400> SEQUENCE: 13
acagtgccct tcagccagac t                                            21

<210> SEQ ID NO 14
<211> LENGTH: 25
<212> TYPE: DNA
<213> ORGANISM: Artificial Sequence
<220> FEATURE:
<223> OTHER INFORMATION: Cerberus R-primer

<400> SEQUENCE: 14
acaactactt tttcacagcc ttcgt                                        25

<210> SEQ ID NO 15
<211> LENGTH: 20
<212> TYPE: DNA
<213> ORGANISM: Artificial Sequence
<220> FEATURE:
<223> OTHER INFORMATION: AFP F-primer
```

```
<400> SEQUENCE: 15
tgcaaacgat gaagcaagag                                              20

<210> SEQ ID NO 16
<211> LENGTH: 20
<212> TYPE: DNA
<213> ORGANISM: Artificial Sequence
<220> FEATURE:
<223> OTHER INFORMATION: AFP R-primer

<400> SEQUENCE: 16
aacaggcctg agaaatctgc                                              20

<210> SEQ ID NO 17
<211> LENGTH: 20
<212> TYPE: DNA
<213> ORGANISM: Artificial Sequence
<220> FEATURE:
<223> OTHER INFORMATION: GATA4 F-primer

<400> SEQUENCE: 17
gtcatctcac tacgggcaca                                              20

<210> SEQ ID NO 18
<211> LENGTH: 18
<212> TYPE: DNA
<213> ORGANISM: Artificial Sequence
<220> FEATURE:
<223> OTHER INFORMATION: GATA4 R-primer

<400> SEQUENCE: 18
cttcagggcc gagaggac                                                18

<210> SEQ ID NO 19
<211> LENGTH: 18
<212> TYPE: DNA
<213> ORGANISM: Artificial Sequence
<220> FEATURE:
<223> OTHER INFORMATION: Sox17 F-primer

<400> SEQUENCE: 19
ggcgcagcag aatccaga                                                18

<210> SEQ ID NO 20
<211> LENGTH: 18
<212> TYPE: DNA
<213> ORGANISM: Artificial Sequence
<220> FEATURE:
<223> OTHER INFORMATION: Sox17 R-primer

<400> SEQUENCE: 20
ccacgacttg cccagcat                                                18

<210> SEQ ID NO 21
<211> LENGTH: 21
<212> TYPE: DNA
<213> ORGANISM: Artificial Sequence
<220> FEATURE:
<223> OTHER INFORMATION: GCM1 F-primer

<400> SEQUENCE: 21
ctctgaagct catcccttgc c                                            21

<210> SEQ ID NO 22
<211> LENGTH: 21
<212> TYPE: DNA
```

```
<213> ORGANISM: Artificial Sequence
<220> FEATURE:
<223> OTHER INFORMATION: GCM1 R-primer

<400> SEQUENCE: 22
tggacgcctt cctggaaaga c                                              21

<210> SEQ ID NO 23
<211> LENGTH: 22
<212> TYPE: DNA
<213> ORGANISM: Artificial Sequence
<220> FEATURE:
<223> OTHER INFORMATION: GATA2 F-primer

<400> SEQUENCE: 23
agaaccgacc actcatcaag cc                                             22

<210> SEQ ID NO 24
<211> LENGTH: 23
<212> TYPE: DNA
<213> ORGANISM: Artificial Sequence
<220> FEATURE:
<223> OTHER INFORMATION: GATA2 R-primer

<400> SEQUENCE: 24
tgctcttctt ggacttgttg gac                                            23

<210> SEQ ID NO 25
<211> LENGTH: 19
<212> TYPE: DNA
<213> ORGANISM: Artificial Sequence
<220> FEATURE:
<223> OTHER INFORMATION: Oct4 F-primer

<400> SEQUENCE: 25
tgggctcgag aaggatgtg                                                 19

<210> SEQ ID NO 26
<211> LENGTH: 20
<212> TYPE: DNA
<213> ORGANISM: Artificial Sequence
<220> FEATURE:
<223> OTHER INFORMATION: Oct4 R-primer

<400> SEQUENCE: 26
gcatagtcgc tgcttgatcg                                                20

<210> SEQ ID NO 27
<211> LENGTH: 20
<212> TYPE: DNA
<213> ORGANISM: Artificial Sequence
<220> FEATURE:
<223> OTHER INFORMATION: Nanog F-primer

<400> SEQUENCE: 27
ccaacatcct gaacctcagc                                                20

<210> SEQ ID NO 28
<211> LENGTH: 20
<212> TYPE: DNA
<213> ORGANISM: Artificial Sequence
<220> FEATURE:
<223> OTHER INFORMATION: Nanog R-primer

<400> SEQUENCE: 28
gctattcttc ggccagttgt                                                20
```

```
<210> SEQ ID NO 29
<211> LENGTH: 20
<212> TYPE: DNA
<213> ORGANISM: Artificial Sequence
<220> FEATURE:
<223> OTHER INFORMATION: beta-actin F-primer

<400> SEQUENCE: 29 gctctttcc agccttcctt                                                  20

<210> SEQ ID NO 30
<211> LENGTH: 20
<212> TYPE: DNA
<213> ORGANISM: Artificial Sequence
<220> FEATURE:
<223> OTHER INFORMATION: beta-actin R-primer

<400> SEQUENCE: 30
cttctgcatc ctgtcagcaa                                                 20
```